(12) United States Patent
Hughes

(10) Patent No.: US 12,416,636 B2
(45) Date of Patent: Sep. 16, 2025

(54) PERSONALIZED TREATMENT OF PANCREATIC CANCER

(71) Applicant: University of Florida Research Foundation, Inc., Gainesville, FL (US)

(72) Inventor: Steven J. Hughes, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 1068 days.

(21) Appl. No.: 17/059,727

(22) PCT Filed: May 31, 2019

(86) PCT No.: PCT/US2019/034889
§ 371 (c)(1),
(2) Date: Nov. 30, 2020

(87) PCT Pub. No.: WO2019/232361
PCT Pub. Date: Dec. 5, 2019

(65) Prior Publication Data
US 2021/0215700 A1 Jul. 15, 2021

Related U.S. Application Data

(60) Provisional application No. 62/678,572, filed on May 31, 2018.

(51) Int. Cl.
*G01N 33/574* (2006.01)
*A61K 45/06* (2006.01)
*A61P 35/00* (2006.01)

(52) U.S. Cl.
CPC ....... *G01N 33/57438* (2013.01); *A61K 45/06* (2013.01); *A61P 35/00* (2018.01); *G01N 33/57484* (2013.01); *G01N 2800/52* (2013.01)

(58) Field of Classification Search
None
See application file for complete search history.

(56) References Cited

U.S. PATENT DOCUMENTS

| | | |
|---|---|---|
| 2012/0040861 A1 | 2/2012 | Williams et al. |
| 2014/0100188 A1* | 4/2014 | Coussens ............ C12Q 1/6886 435/6.12 |

FOREIGN PATENT DOCUMENTS

WO 2015164772 A1 10/2015

OTHER PUBLICATIONS

Yu, 2010, Clin. Chem, pp. 376-387.*
Human Cytokine/Chemokin Magnetic Bead Panel, 2013, pp. 1-32.*
Petrushnko, 2016, HPB, vol. 18: 652-663.*
Grizzle, 2010, Cancer Res. vol. 70: 2732.*
Chen, 2013, Pancreatlogy, vol. 13: 298-304.*
Chang, 2009, Gast. Endos. vol. 69: S157-S158.*
International Search Report issued for PCT/US2019/034889, mailed Aug. 15, 2019.
Delitto et al., The Inflammatory Milieu Within the Pancreatic Cancer Microenvironment Correlates with Clinicopathologic Parameters, Chemoresistance and Survival, BMC Cancer, vol. 15, No. 783, p. 1-10, 2015.
Brand et al., A MicroRNA-Based Test Improves Endoscopic Ultrasound-Guided Cytologic Diagnosis of Pancreatic Cancer, Clinical Gastroenterology and Hepatology, vol. 12, No. 10, p. 1717-1723, 2014.
Liou et al., The Presence of Interleukin-13 at Pancreatic ADM/PanIn Lesions Alters Macrophage Populations and Mediates Pancreatic Tumorigenesis, Cell Reports, vol. 19, No. 7, p. 1322-1333, 2017.
Van Audenaerde et al., Interleukin-15 Stimulates Natural Killer Cell-Mediated Killing of Both Human Pancreatic Cancer and Stellate Cells, vol. 8, No. 34, p. 56968-56979, 2017.
Turner et al., Diagnosis of pancreatic neoplasia with EUS and FNA: a report of accuracy. Gastrointest Endosc; 71(1):91-8, 2010.
Chen et al., Diagnostic accuracy of endoscopic ultrasound-guided fineneedle aspiration for pancreatic cancer: a meta-analysis, Pancreatology;13(3):298-304, 2013.
Eloubeidi et al., Endoscopic ultrasound-guided fine needle aspiration biopsy of patients with suspected pancreatic cancer: diagnostic accuracy and acute and 30-day complications. Am J Gastroenterol.; 98(12):2663-8, 2003.
Shin et al., Endoscopic ultrasound-guided fine-needle aspiration in 179 cases: the M. D. Anderson Cancer Center experience. Cancer, 96(3):174-80, 2002.
Youngwirth et al., Nationwide trends and outcomes associated with neoadjuvant therapy in pancreatic cancer: An analysis of 18 243 patients. J Surg Oncol., 116(2):127-32, 2017.
Yamabe et al., Efforts to improve the diagnostic accuracy of endoscopic ultrasound-guided fine-needle aspiration for pancreatic tumors. Endosc Ultrasound, 5(4):225-32, 2016.
Storm et al., Endoscopic ultrasound-guided techniques for diagnosing pancreatic mass lesions: Can we do better? World J Gastroenterol., 22(39):8658-69, 20016.
Cazacu et al., A quarter century of EUS-FNA: Progress, milestones, and future directions. Endosc Ultrasound, 7(3):141-60, 2018.
Collins et al., Rapid on-site evaluation for endoscopic ultrasound-guided fine-needle biopsy of the pancreas decreases the incidence of repeat biopsy procedures. Cancer Cytopathol, 121(9):518-24, 2013.
Schmidt et al., Rapid on-site evaluation increases endoscopic ultrasound-guided fine-needle aspiration adequacy for pancreatic lesions. Dig Dis Sci., 58(3):872-82, 2013.
Kongkam et al., Combination of EUS-FNA and elastography (strain ratio) to exclude malignant solid pancreatic lesions: A prospective singleblinded study. J Gastroenterol Hepatol., 30(11):1683-9, 2015.
Reicher et al., Fluorescence in situ hybridization and K-ras analyses improve diagnostic yield of endoscopic ultrasound-guided fine-needle aspiration of solid pancreatic masses. Pancreas., 40(7):1057-62, 2011.

(Continued)

*Primary Examiner* — Amy E Juedes
(74) *Attorney, Agent, or Firm* — THOMAS|HORSTEMEYER, LLP

(57) ABSTRACT

Disclosed herein is a soluble protein signature from the tumor microenvironment that can predict overall survival post-surgery in pancreatic adenocarcinoma. The disclosed protein signatures provide a precision approach to surgical therapy for patients with pancreatic cancer. Also disclosed herein is a soluble protein signature from the tumor microenvironment that can diagnose pancreatic ductal adenocarcinoma (PDAC). Also disclosed herein are proteins that can be used to accurately normalize protein levels in a pancreatic sample.

6 Claims, 31 Drawing Sheets

(56) References Cited

OTHER PUBLICATIONS

Rodriguez et al., RNA sequencing distinguishes benign from malignant pancreatic lesions sampled by EUS-guided FNA. Gastrointest Endosc., 84(2):252-8, 2016.

Szafranska et al., Analysis of microRNAs in pancreatic fine-needle aspirates can classify benign and malignant tissues. Clin Chem., 54(10):1716-24, 2008.

Chu et al., Stromal biology of pancreatic cancer. J Cell Biochem., 101(4):887-907, 2007.

Campbell-Thompson et al., Network for Pancreatic Organ Donors with Diabetes (nPOD): developing a tissue biobank for type 1 diabetes. Diabetes Metab Res Rev., 28(7):608-17, 2012.

Liu et al., Type 1 diabetes cadaveric human pancreata exhibit a unique exocrine tissue proteomic profile. Proteomics., 16(9):1432-46, 2016.

R Core Team (2018). R: A language and environment for statistical computing. R Foundation for Statistical Computing V, Austria. URL https://www.R-project.org/).

Jelle J. Goeman (2018). Penalized R package, version 0.9-51. URL https://CRAN.Rproject. org/package=penalized.

Burnett et al., Sensitivity of alternative testing for pancreaticobiliary cancer: a 10-y review of the literature. J Surg Res., 190(2):535-47, 2014.

Senoo et al., Immunohistochemical analysis of IMP3 and p53 expression in endoscopic ultrasound-guided fine needle aspiration and resected specimens of pancreatic diseases. Pancreatology., 8(2):176-83, 2018.

Mei et al., EUS elastography for diagnosis of solid pancreatic masses: a meta-analysis. Gastrointest Endosc., 77(4):578-89, 2013.

Brand et al., A microRNA-based test improves endoscopic ultrasound-guided cytologic diagnosis of pancreatic cancer. Clin Gastroenterol Hepatol., 12(10):1717-23, 2014.

Frampton et al., Prospective validation of microRNA signatures for detecting pancreatic malignant transformation in endoscopic-ultrasound guided fine-needle aspiration biopsies. Oncotarget., 10;7(19):28556-69, 2016.

Yoon et al., Inadequate cytology in thyroid nodules: should we repeat aspiration or follow-up? Ann Surg Oncol., 18(5):1282-9, 2011.

Bartolazzi et al., Application of an immunodiagnostic method for improving preoperative diagnosis of nodular thyroid lesions. Lancet., 26;357(9269):1644-50, 2001.

Cantara et al., Molecular Signature of Indeterminate Thyroid Lesions: Current Methods to Improve Fine Needle Aspiration Cytology (FNAC) Diagnosis. Int J Mol Sci., 18(4), 2017.

Jin et al., A 2-Protein Signature Predicting Clinical Outcome in High-Grade Serous Ovarian Cancer. Int J Gynecol Cancer., 28(1):51-8, 2018.

Muinao et al., Diagnostic and Prognostic Biomarkers in ovarian cancer and the potential roles of cancer stem cells—An updated review. Exp Cell Res., 362(1):1-10, 2018.

Trachana et al., The Development of an Angiogenic Protein "Signature" in Ovarian Cancer Ascites as a Tool for Biologic and Prognostic Profiling. PLoS One., 11(6):e0156403, 2016.

Gocheva et al., Quantitative proteomics identify Tenascin-C as a promoter of lung cancer progression and contributor to a signature prognostic of patient survival. Proc Natl Acad Sci U S A., 114(28):E5625-E34, 2017.

Lee et al., Development and Validation of a Novel Plasma Protein Signature for Breast Cancer Diagnosis by Using Multiple Reaction Monitoring-based Mass Spectrometry. Anticancer Res., 35(11):6271-9, 2015.

Skoog et al., Tumor tissue protein signatures reflect histological grade of breast cancer. PLoS One., 12(6):e0179775, 2017.

Poch et al., Systemic immune dysfunction in pancreatic cancer patients. Langenbecks Arch Surg., 392(3):353-8, 2007.

Wang et al., From Friend to Enemy: Dissecting the Functional Alteration of Immunoregulatory Components during Pancreatic Tumorigenesis. Int J Mol Sci., 19(11), 2018.

Zhuang et al., IL1 Receptor Antagonist Inhibits Pancreatic Cancer Growth by Abrogating NF-kappaB Activation. Clin Cancer Res., 22(6):1432-44, 2016.

\* cited by examiner

PERSONALIZED TREATMENT OF PANCREATIC CANCER

CROSS-REFERENCE TO RELATED APPLICATIONS

This application is a National Stage of International Application No. PCT/US2019/034889, filed May 31, 2019, which claims benefit of U.S. Provisional Application No. 62/678,572, filed May 31, 2018, which is hereby incorporated herein by reference in its entirety.

STATEMENT REGARDING FEDERALLY SPONSORED RESEARCH OR DEVELOPMENT

This invention was made with Government Support under Grant No. DK108320 awarded by the National Institutes of Health. The Government has certain rights in the invention.

BACKGROUND

Approximately 20% of patients diagnosed with pancreatic ductal adenocarcinoma (PDAC) have localized disease by contemporary imaging modalities and qualify for surgical resection with the intent of cure. Even then, the median overall survival rate after resection is only 15 months producing a 27% 5-year survival rate. Presently, the best predictor for overall survival after pancreatectomy remains TNM staging. Data also support positive surgical margin, need for major vascular resection, positive lymph node ratio, serum CA19-9 levels, and invasiveness properties as negative prognostic variables (Berger A C, et al. J Clin Oncol 2008 26(36):5918-22; Distier M, et al. BMC surgery. 2013 13:12; Murakami Y, et al. World J Surg. 2015 39(9):2306-14). These prognostic factors are incorporated into modern surgical decision-making, but of them, only the serum CA19-9 level is objectively known in the preoperative setting, and this variable also has its limitations.

Survival data indicate some PDAC patients suffer early disease progression following surgery, essentially denying them from any benefit (Delitto D, et al. Pharmacol Ther. 2016 166:9-29; Baxter N N, et al. Ann Surg Oncol. 2007 14(4):1320-6). Essentially, PDAC is a biologically diverse disease that cannot be characterized by TNM staging alone (Waddell N, et al. Nature. 2015 518(7540):495-501; Bailey P, et al. Nature. 2016 531(7592):47-52). This genomic diversity can be broadly classified into four different subsets of PDAC that associate with prognosis, independent of stage (Bailey P, et al. Nature. 2016 531(7592):47-52). Methods are needed that can accurately predict the potential benefit of surgical therapy for PDAC.

The gold standard for diagnosis of a pancreatic mass remains endoscopic ultrasound-guided fine needle aspiration (EUS-guided FNA). EUS-guided FNA fails to provide definitive diagnosis in 15-25% of patients ultimately found to have pancreatic ductal adenocarcinoma (PDAC) [Turner, B. G., et al., Gastrointest Endosc, 2010. 71(1):91-8; Chen, G., et al., Pancreatology, 2013. 13(3):298-304; Eloubeidi, M. A., et al., Am J Gastroenterol, 2003. 98(12):2663-8; Shin, H. J., et al., Cancer, 2002. 96(3):174-80]. This is due to inadequate specimens, atypical/suspicious but non-diagnostic cytology, technical failure, and false negative results. This can have tremendous implications for patients. Aside from the stress associated with a possible cancer diagnosis, failure to diagnose PDAC can lead to repeat procedures for cytology, missed cancers, disease progression, delays in treatment, and exclusion from clinical trials. As neoadjuvant therapy becomes more common place, the ability to obtain adequate tissue for diagnosis becomes more critical [Youngwirth, L. M., et al., J Surg Oncol, 2017. 116(2):127-132].

Highlighting the problem is a large volume of literature suggesting variations in sampling technique. Clinical trials have evaluated needle type and gauge, number of needle passes, stylet use, use of suction, and presence of on-site cytopathology to determine best practices [Yamabe, A., et al., Endosc Ultrasound, 2016. 5(4):225-32; Storm, A. C. and L. S. Lee, World J Gastroenterol, 2016. 22(39):8658-8669; Cazacu, I. M., et al., Endosc Ultrasound, 2018. 7(3):141-160; Collins, B. T., et al., Cancer Cytopathol, 2013. 121(9):518-24; Schmidt, R. L., et al., Dig Dis Sci, 2013. 58(3):872-82]. These methods focus on obtaining an adequate sample for a cytopathologist to make a diagnosis. Supplementary tests to cytopathology may improve the diagnostic capability of EUS-guided FNA. Elastography, fluorescence in situ hybridization (FISH), K-RAS analysis, microRNAs (miRNA), immunostaining, and RNAseq analysis have all been proposed as supplementary tests to cytopathology but none have gained widespread use [Kongkam, P., et al., J Gastroenterol Hepatol, 2015. 30(11):1683-9; Reicher, S., et al., Pancreas, 2011. 40(7):1057-62; Rodriguez, S. A., et al., Gastrointest Endosc, 2016. 84(2):252-8; Szafranska, A. E., et al., Clin Chem, 2008. 54(10):1716-24].

SUMMARY

Disclosed herein is a soluble protein signature from the tumor microenvironment that can predict overall survival post-surgery in pancreatic adenocarcinoma. The disclosed protein signatures provide a precision approach to surgical therapy for patients with pancreatic cancer.

In particular, disclosed herein is a method for predicting survival of a subject with pancreatic ductal adenocarcinoma (PDAC) that involves assaying a tumor microenvironment sample from the subject for soluble immune proteins levels. A survival score can then be calculated based on the expression levels of one or more soluble immune protein selected from the group comprising Eotaxin, FGF-2, G-CSF, IL-4, IP-10, PDGF-AA, and TNFα, wherein the survival score is indicative of post-surgical survival. The method can further involve selecting a suitable treatment, such as surgery or palliative care, for the subject based on the survival score.

Therefore, also disclosed is a method for treating a subject for PDAC that involves calculating a survival score based on a signature of expression levels of any 2, 3, 4, 5, 6, or 7 of the soluble immune proteins selected from the group comprising Eotaxin, FGF-2, G-CSF, IL-4, IP-10, PDGF-AA, and TNFα, that is indicative of prolonged post-surgical survival, and surgically resecting the PDAC from the subject.

Likewise, also disclosed is a method for treating a subject for PDAC that involves calculating a survival score based on a signature of expression levels of any 2, 3, 4, 5, 6, or 7 of the soluble immune proteins selected from the group comprising Eotaxin, FGF-2, G-CSF, IL-4, IP-10, PDGF-AA, and TNFα, that is not indicative of prolonged post-surgical survival, and treating the subject with something other than surgical resection, such as palliative care, chemotherapy, hormone therapy, and/or radiotherapy.

The survival score can be calculated using standard statistical techniques, including univariate and multivariate methods. In particular embodiments, the survival score is calculated using a multivariate analysis.

The tumor microenvironment sample can be obtained using standard techniques, such as by a fine needle aspiration (FNA) biopsy of the pancreatic cancer.

The subject of the method can in some cases be any subject diagnosed or suspected of having PDAC. In some cases, the subject previously received treatment for the PDAC, including portal vein resection, chemotherapy, hormone therapy, and/or radiation therapy. In other embodiments, the subject has received no prior therapy.

The disclosed method can be used alone or with other prognostic factors to predict survival. In some cases, the disclosed protein signatures are able to predict post-surgical survival for a subset of subjects that current prognostic factors don't identify. In some embodiments, the disclose protein signatures are used in combination with prognostic factors, such as tumor stage, surgical margin, perineural invasion, performance status (PS), treatment effect, CEA levels, serum CA19-9 levels, and TNM stage.

Elevated levels of CA 19-9 and CEA are known to predict increased chances of inoperability and poor survival in pancreatic tumors. For example, a Ca19-9 level greater than 1000 U/ml is ominous for occult metastatic disease and associates with poor prognosis. In some embodiments, the subject does not have elevated serum CEA and/or CA19-9 levels, but the disclosed protein signatures identify the subject as having a poor post-surgical survival. In other embodiments, the subject has elevated serum CEA and/or CA19-9 levels, but the disclosed protein signatures identify the subject as a candidate for surgical resection.

In some aspects, there are two opportunities to use the disclosed protein signatures to predict survival. The first is with patients that appear to be candidates for surgery based upon imaging. The second opportunity is after surgery, when N stage, LN ration, margin status, invasive properties, can be added to the protein signature to calculate the survival score. For example, LN ratio and portal vein involvement provide additional prognostic information in combination with the protein signatures.

Also disclosed is a kit for precision pancreatic cancer surgical therapy, comprising antibodies that selectively bind human Eotaxin, antibodies that selectively bind FGF-2, antibodies that selectively bind G-CSF, antibodies that selectively bind IL-4, antibodies that selectively bind IP-10, antibodies that selectively bind PDGF-AA, and antibodies that selectively bind TNFα.

Also disclosed herein is a method for diagnosing a subject for pancreatic ductal adenocarcinoma (PDAC) that involves assaying a tumor microenvironment sample from the subject for soluble immune proteins levels; and calculating a risk score based on differential expression of 1, 2, 3, 4, 5, 6, 7, 8, 9, 10, 11 or more soluble immune protein selected from GRO, Ftl-3L, IL-15, PDGF-AA, Fractalkine, TGF-α, IL-10, IL-6, IL-1A, IP-10, IL-8, and IL-RA, or any combination thereof. In particular, the risk score can be based on differential expression of at least IL-1RA, GRO, or a combination thereof. In some embodiments, all of GRO, Ftl-3L, IL-15, PDGF-AA, Fractalkine, TGF-α, IL-10, IL-6, IL-1A, IP-10, IL-8, and IL-RA are used to calculate the risk score.

The risk score can be calculated using standard statistical models and machine learning based on the data provided. Herein, in some embodiments, the score diagnoses PDAC, and the method further comprise surgically resecting the PDAC from the subject. This risk score can in some embodiments function in lieu of cytologic confirmation of PDAC for other clinical decisions, including the recommendation of chemotherapy, radiation therapy, or enrollment in a clinical trial.

A kit for diagnosing pancreatic ductal adenocarcinoma (PDAC), comprising antibodies that selectively bind 1, 2, 3, 4, 5, 6, 7, 8, 9, 10 or more of human GRO, Ftl-3L, IL-15, PDGF-AA, Fractalkine, TGF-α, IL-10, IL-6, IL-1A, IP-10, IL-8, and IL-RA.

In each of the above methods, the amount of detected soluble immune protein in the sample can be normalized using standard methods, such as total protein, Quantile, Baseline, and LOESS normalization. However, most normalization methods make two basic assumptions about the data: 1) only a few genes are over-expressed or under-expressed in one array relative to the others, and 2) the number of genes over-expressed in a condition is similar to the number of genes under-expressed. As disclosed herein PDGF-BB, IL-13, and IL-15 levels remain consistent in benign and cancerous pancreatic tissue samples. Therefore, in some embodiments, the amount of detected soluble immune protein in the sample can be normalized using the amount of PDGF-BB, IL-13, IL-15, or any combination thereof, in the sample.

Since this normalization method could in some embodiments be used with any pancreatic tissue assay, also disclosed is a method for measuring expression of a candidate protein in a pancreatic sample that involves assaying the sample for protein levels of the candidate protein and one or more of PDGF-BB, IL-13, and IL-15; and normalizing the amount of detected candidate protein using the amount of detected PDGF-BB, IL-13, IL-15, or any combination thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

In FIG. 3A shows a low risk group with a median survival of 24 months and a high risk group with a median survival of 7 months. Gray areas around each curve indicate the 95% confidence interval. FIG. 3B shows predicted survival curves for the indicated percentile of the Protein Risk Score.

FIG. 4A shows survival curves for all 36 patients, all 26 patients who did not receive neoadjuvant therapy, and all 10 patients who received neoadjuvant therapy (green). FIG. 4B show low risk and high risk groups with neoadjuvant patients excluded from each maintain significant differences in overall survival. Gray areas around each curve represents 95% confidence intervals. All p-values calculated using the log-rank test.

DETAILED DESCRIPTION

Figure 1:
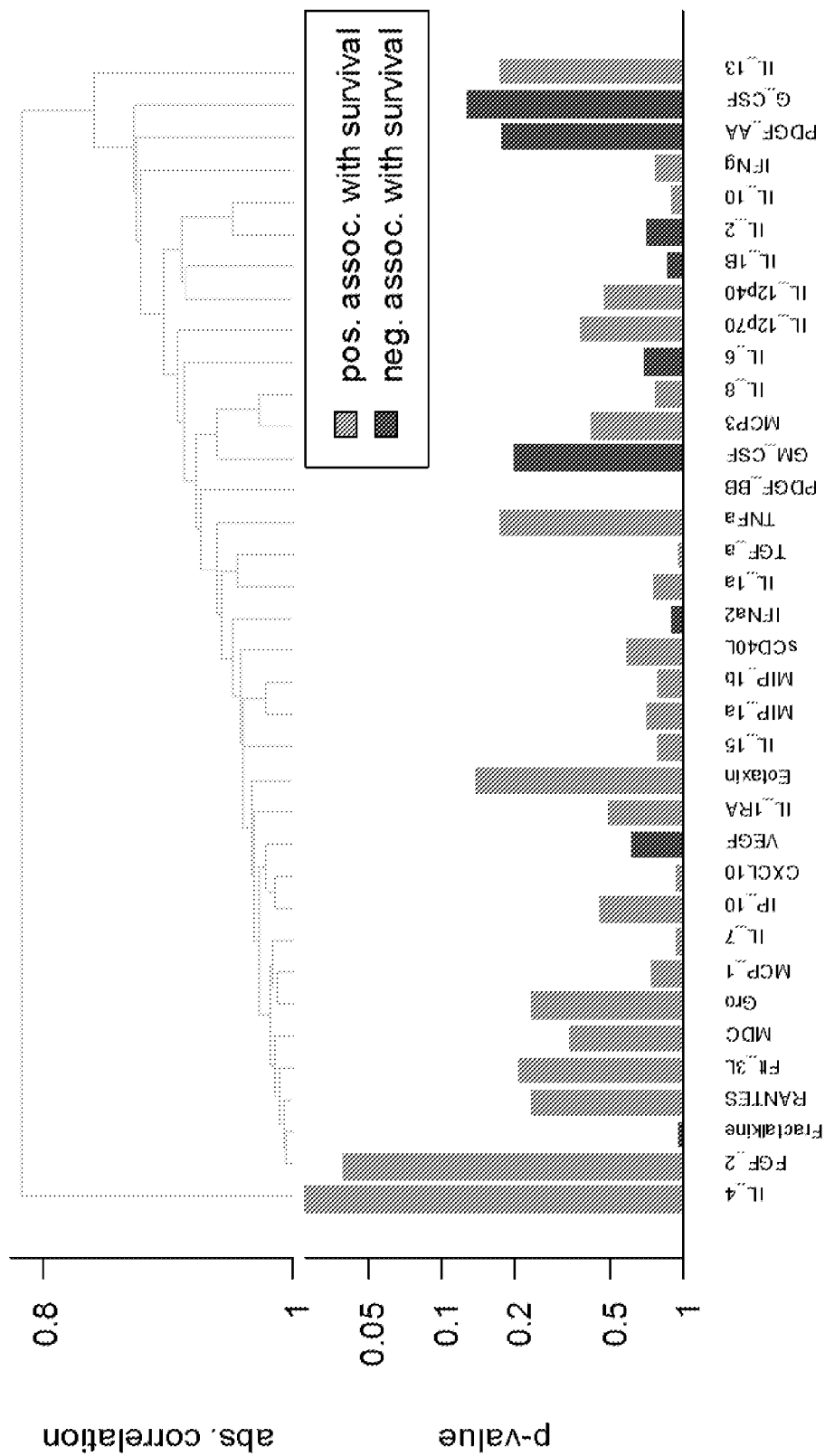
FIG. 1 shows analyte associations with overall survival. Analytes on x-axis graphed against its associated p-value on y-axis with green indicating a positive correlation with overall survival and red indicating a negative correlation with overall survival. Hierarchical clustering based on associations between analytes.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

Prognosis Protein Signatures

Disclosed herein are protein signatures that can predict post-surgical survival in subjects with PDAC. As disclosed herein, Eotaxin, FGF-2, IL-4, IP-10, and TNFα expression levels in the tumor microenvironment positively correlate with good post-surgical survival, and G-CSF and PDGF-AA expression levels in the tumor microenvironment negatively correlate with poor post-surgical survival.

Any combination of the disclosed proteins can be used as a protein signature. In some embodiments, the protein signature involves Eotaxin, FGF-2, IL-4, IP-10, TNFα, G-CSF, and PDGF-AA.

In some embodiments, the protein signature involves Eotaxin, FGF-2, IL-4, IP-10, TNFα, and G-CSF. In some embodiments, the protein signature involves Eotaxin, FGF-2, IL-4, IP-10, TNFα, and PDGF-AA. In some embodiments, the protein signature involves Eotaxin, FGF-2, IL-4, IP-10, G-CSF, and PDGF-AA. In some embodiments, the protein signature involves Eotaxin, FGF-2, IL-4, TNFα, G-CSF, and PDGF-AA. In some embodiments, the protein signature involves Eotaxin, FGF-2, IL-4, IP-10, TNFα, G-CSF, and PDGF-AA. In some embodiments, the protein signature involves Eotaxin, FGF-2, IP-10, TNFα, and G-CSF, and PDGF-AA. In some embodiments, the protein signature involves Eotaxin, IL-4, IP-10, TNFα, G-CSF, and PDGF-AA. In some embodiments, the protein signature involves FGF-2, IL-4, IP-10, TNFα, G-CSF, and PDGF-AA.

In some embodiments, the protein signature involves Eotaxin, FGF-2, IL-4, IP-10, and TNFα. In some embodiments, the protein signature involves Eotaxin, FGF-2, IL-4, IP-10, and G-CSF. In some embodiments, the protein signature involves Eotaxin, FGF-2, IL-4, TNFα, and G-CSF. In some embodiments, the protein signature involves Eotaxin, FGF-2, IP-10, TNFα, and G-CSF. In some embodiments, the protein signature involves Eotaxin, IL-4, IP-10, TNFα, and G-CSF. In some embodiments, the protein signature involves FGF-2, IL-4, IP-10, TNFα, and G-CSF. In some embodiments, the protein signature involves Eotaxin, FGF-2, IL-4, IP-10, and PDGF-AA. In some embodiments, the protein signature involves Eotaxin, FGF-2, IL-4, TNFα, and PDGF-AA. In some embodiments, the protein signature involves Eotaxin, FGF-2, IP-10, TNFα, and PDGF-AA. In some embodiments, the protein signature involves Eotaxin, IL-4, IP-10, TNFα, and PDGF-AA. In some embodiments, the protein signature involves FGF-2, IL-4, IP-10, TNFα, and PDGF-AA. In some embodiments, the protein signature involves Eotaxin, FGF-2, IL-4, G-CSF, and PDGF-AA. In some embodiments, the protein signature involves Eotaxin, FGF-2, IP-10, G-CSF, and PDGF-AA. In some embodiments, the protein signature involves Eotaxin, IL-4, IP-10, G-CSF, and PDGF-AA. In some embodiments, the protein signature involves FGF-2, IL-4, IP-10, G-CSF, and PDGF-AA. In some embodiments, the protein signature involves Eotaxin, FGF-2, TNFα, G-CSF, and PDGF-AA. In some embodiments, the protein signature involves Eotaxin, IL-4, TNFα, G-CSF, and PDGF-AA. In some embodiments, the protein signature involves FGF-2, IL-4, TNFα, G-CSF, and PDGF-AA. In some embodiments, the protein signature involves Eotaxin, IP-10, TNFα, G-CSF, and PDGF-AA. In some embodiments, the protein signature involves FGF-2, IP-10, TNFα, G-CSF, and PDGF-AA.

In some embodiments, the protein signature involves Eotaxin, FGF-2, IL-4, and IP-10. In some embodiments, the protein signature involves Eotaxin, FGF-2, IL-4, and TNFα. In some embodiments, the protein signature involves Eotaxin, FGF-2, IP-10, and TNFα. In some embodiments, the protein signature involves Eotaxin, IL-4, IP-10, and TNFα. In some embodiments, the protein signature involves FGF-2, IL-4, IP-10, and TNFα. In some embodiments, the protein signature involves Eotaxin, FGF-2, IL-4, and G-CSF. In some embodiments, the protein signature involves Eotaxin, FGF-2, IP-10, and G-CSF. In some embodiments, the protein signature involves Eotaxin, IL-4, IP-10, and G-CSF. In some embodiments, the protein signature involves FGF-2, IL-4, IP-10, and G-CSF. In some embodiments, the protein signature involves Eotaxin, FGF-2, TNFα, and G-CSF. In some embodiments, the protein signature involves Eotaxin, IL-4, TNFα, and G-CSF. In some embodiments, the protein signature involves FGF-2, IL-4, TNFα, and G-CSF. In some embodiments, the protein signature involves Eotaxin, IP-10, TNFα, and G-CSF. In some embodiments, the protein signature involves FGF-2, IP-10, TNFα, and G-CSF. In some embodiments, the protein signature involves Eotaxin, FGF-2, IL-4, and PDGF-AA In some embodiments, the protein signature involves Eotaxin, FGF-2, IP-10, and PDGF-AA. In some embodiments, the protein signature involves Eotaxin, IL-4, IP-10, and PDGF-AA. In some embodiments, the protein signature involves FGF-2, IL-4, IP-10, and PDGF-AA. In some embodiments, the protein signature involves Eotaxin, FGF-2, TNFα, and PDGF-AA. In some embodiments, the protein signature involves Eotaxin, IL-4, TNFα, and PDGF-AA. In some embodiments, the protein signature involves FGF-2, IL-4, TNFα, and PDGF-AA. In some embodiments, the protein signature involves Eotaxin, IP-10, TNFα, PDGF-AA. In some embodiments, the protein signature involves FGF-2, IP-10, TNFα, and PDGF-AA. In some embodiments, the protein signature involves Eotaxin, FGF-2, G-CSF, and PDGF-AA. In some embodiments, the protein signature involves Eotaxin, IL-4, G-CSF, and PDGF-AA. In some embodiments, the protein signature involves FGF-2, IL-4, G-CSF, and PDGF-AA. In some embodiments, the protein signature involves Eotaxin, TNFα, G-CSF, and PDGF-AA. In some embodiments, the protein signature involves FGF-2, TNFα, G-CSF, and PDGF-AA. In some embodiments, the protein signature involves IP-10, TNFα, G-CSF, and PDGF-AA.

In some embodiments, the protein signature involves Eotaxin, FGF-2, and IL-4. In some embodiments, the protein signature involves Eotaxin, FGF-2, and IP-10. In some embodiments, the protein signature involves Eotaxin, FGF-2, and TNFα. In some embodiments, the protein signature involves Eotaxin, FGF-2, and G-CSF. In some embodiments, the protein signature involves Eotaxin, FGF-2, and PDGF-AA. In some embodiments, the protein signature involves Eotaxin, IL-4, and IP-10. In some embodiments, the protein signature involves Eotaxin, IL-4, and TNFα. In some embodiments, the protein signature involves Eotaxin, IL-4, and G-CSF. In some embodiments, the protein signature involves Eotaxin, IL-4, and PDGF-AA. In some embodiments, the protein signature involves Eotaxin, IP-10, and TNFα. In some embodiments, the protein signature involves Eotaxin, IP-10, and G-CSF. In some embodiments, the protein signature involves Eotaxin, IP-10, and PDGF-AA. In some embodiments, the protein signature involves Eotaxin, TNFα, and G-CSF. In some embodiments, the protein signature involves Eotaxin, TNFα, and PDGF-AA. In some embodiments, the protein signature involves FGF-2, IL-4, and IP-10. In some embodiments, the protein signature involves FGF-2, IL-4, and TNFα. In some embodiments, the protein signature involves FGF-2, IL-4, and G-CSF. In some embodiments, the protein signature involves FGF-2, IL-4, and PDGF-AA. In some embodiments, the protein signature involves FGF-2, IP-10, and TNFα. In some embodiments, the protein signature involves FGF-2, IP-10, and G-CSF. In some embodiments, the protein signature involves FGF-2, IP-10, and PDGF-AA. In some embodiments, the protein signature involves FGF-2, TNFα, and G-CSF. In some embodiments, the protein signature involves FGF-2, TNFα, and PDGF-AA. In some embodiments, the protein signature involves FGF-2, G-CSF, and PDGF-AA. In some embodiments, the protein signature involves IL-4, IP-10, and TNFα. In some embodiments, the protein signature involves IL-4, IP-10, and G-CSF. In some embodiments, the protein signature involves IL-4, IP-10, and PDGF-AA. In some embodiments, the protein signature involves IL-4, TNFα, and G-CSF. In some embodiments, the protein signature involves IL-4, TNFα, and PDGF-AA. In some embodiments, the protein signature involves IL-4, G-CSF, and PDGF-AA.

In some embodiments, the method involves assaying a tumor microenvironment sample from the subject for one or more of these proteins. Techniques for measuring protein levels are known and include immunoassays. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Diagnosis Protein Signatures

Disclosed herein are protein signatures that can diagnose PDAC. As disclosed herein, GRO, Ftl-3L, IL-15, PDGF-AA, and Fractalkine expression levels in the tumor microenvironment negatively correlate with PDAC, and elevated TGF-α, IL-10, IL-6, IL-1A, IP-10, IL-8, and IL-RA expression levels in the tumor microenvironment positively correlate with PDAC. Any combination of the disclosed proteins can be used as a protein signature. In some embodiments, the protein signature involves 1, 2, 3, 4, 5, 6, 7, 8, 9, 10, 11 or more soluble immune protein selected from GRO, Ftl-3L, IL-15, PDGF-AA, Fractalkine, TGF-α, IL-10, IL-6, IL-1A, IP-10, IL-8, and IL-RA.

In some embodiments, the protein signature involves Ftl-3L, IL-15, PDGF-AA, Fractalkine, TGF-α, IL-10, IL-6, IL-1A, IP-10, IL-8, and IL-RA. In some embodiments, the protein signature involves GRO, IL-15, PDGF-AA, Fractalkine, TGF-α, IL-10, IL-6, IL-1A, IP-10, IL-8, and IL-RA. In some embodiments, the protein signature involves GRO, Ftl-3L, PDGF-AA, Fractalkine, TGF-α, IL-10, IL-6, IL-1A, IP-10, IL-8, and IL-RA. In some embodiments, the protein signature involves GRO, Ftl-3L, IL-15, Fractalkine, TGF-α, IL-10, IL-6, IL-1A, IP-10, IL-8, and IL-RA. In some embodiments, the protein signature involves GRO, Ftl-3L, IL-15, PDGF-AA, TGF-α, IL-10, IL-6, IL-1A, IP-10, IL-8, and IL-RA. In some embodiments, the protein signature involves GRO, Ftl-3L, IL-15, PDGF-AA, Fractalkine, IL-10, IL-6, IL-1A, IP-10, IL-8, and IL-RA. In some embodiments, the protein signature involves GRO, Ftl-3L, IL-15, PDGF-AA, Fractalkine, TGF-α, IL-6, IL-1A, IP-10, IL-8, and IL-RA. In some embodiments, the protein signature involves GRO, Ftl-3L, IL-15, PDGF-AA, Fractalkine, TGF-α, IL-10, IL-1A, IP-10, IL-8, and IL-RA. In some embodiments, the protein signature involves GRO, Ftl-3L, IL-15, PDGF-AA, Fractalkine, TGF-α, IL-10, IL-6, IP-10, IL-8, and IL-RA. In some embodiments, the protein signature involves GRO, Ftl-3L, IL-15, PDGF-AA, Fractalkine, TGF-α, IL-10, IL-6, IL-1A, IL-8, and IL-RA. In some embodiments, the protein signature involves GRO, Ftl-3L, IL-15, PDGF-AA, Fractalkine, TGF-α, IL-10, IL-6, IL-1A, IP-10, and IL-RA. In some embodiments, the protein signature involves GRO, Ftl-3L, IL-15, PDGF-AA, Fractalkine, TGF-α, IL-10, IL-6, IL-1A, IP-10, and IL-8.

In some embodiments, the protein signature involves IL-15, PDGF-AA, Fractalkine, TGF-α, IL-10, IL-6, IL-1A, IP-10, IL-8, and IL-RA. In some embodiments, the protein signature involves Ftl-3L, PDGF-AA, Fractalkine, TGF-α, IL-10, IL-6, IL-1A, IP-10, IL-8, and IL-RA. In some embodiments, the protein signature involves Ftl-3L, IL-15, Fractalkine, TGF-α, IL-10, IL-6, IL-1A, IP-10, IL-8, and IL-RA. In some embodiments, the protein signature involves Ftl-3L, IL-15, PDGF-AA, TGF-α, IL-10, IL-6, IL-1A, IP-10, IL-8, and IL-RA. In some embodiments, the protein signature involves Ftl-3L, IL-15, PDGF-AA, Fractalkine, IL-10, IL-6, IL-1A, IP-10, IL-8, and IL-RA. In some embodiments, the protein signature involves Ftl-3L, IL-15, PDGF-AA, Fractalkine, TGF-α, IL-6, IL-1A, IP-10, IL-8, and IL-RA. In some embodiments, the protein signature involves Ftl-3L, IL-15, PDGF-AA, Fractalkine, TGF-α, IL-10, IL-1A, IP-10, IL-8, and IL-RA. In some embodiments, the protein signature involves Ftl-3L, IL-15, PDGF-AA, Fractalkine, TGF-α, IL-10, IL-6, IP-10, IL-8, and IL-RA. In some embodiments, the protein signature involves Ftl-3L, IL-15, PDGF-AA, Fractalkine, TGF-α, IL-10, IL-6, IL-1A, IL-8, and IL-RA. In some embodiments, the protein signature involves Ftl-3L, IL-15, PDGF-AA, Fractalkine, TGF-α, IL-10, IL-6, IL-1A, IP-10, and IL-RA. In some embodiments, the protein signature involves Ftl-3L, IL-15, PDGF-AA, Fractalkine, TGF-α, IL-10, IL-6, IL-1A, IP-10, and IL-8.

In some embodiments, the protein signature involves IL-15, PDGF-AA, Fractalkine, TGF-α, IL-10, IL-6, IL-1A, IP-10, IL-8, and IL-RA. In some embodiments, the protein signature involves GRO, PDGF-AA, Fractalkine, TGF-α, IL-10, IL-6, IL-1A, IP-10, IL-8, and IL-RA. In some embodiments, the protein signature involves GRO, IL-15, Fractalkine, TGF-α, IL-10, IL-6, IL-1A, IP-10, IL-8, and IL-RA. In some embodiments, the protein signature involves GRO, IL-15, PDGF-AA, TGF-α, IL-10, IL-6, IL-1A, IP-10, IL-8, and IL-RA. In some embodiments, the protein signature involves GRO, IL-15, PDGF-AA, Fractalkine, IL-10, IL-6, IL-1A, IP-10, IL-8, and IL-RA. In some embodiments, the protein signature involves GRO, IL-15, PDGF-AA, Fractalkine, TGF-α, IL-6, IL-1A, IP-10, IL-8, and IL-RA. In some embodiments, the protein signature involves GRO, IL-15, PDGF-AA, Fractalkine, TGF-α, IL-10, IL-1A, IP-10, IL-8, and IL-RA. In some embodiments, the protein signature involves GRO, IL-15, PDGF-AA, Fractalkine, TGF-α, IL-10, IL-6, IP-10, IL-8, and IL-RA. In some embodiments, the protein signature involves GRO, IL-15, PDGF-AA, Fractalkine, TGF-α, IL-10, IL-6, IL-1A, IL-8, and IL-RA. In some embodiments, the protein signature involves GRO, IL-15, PDGF-AA, Fractalkine, TGF-α, IL-10, IL-6, IL-1A, IP-10, and IL-RA. In some embodiments, the protein signature involves GRO, IL-15, PDGF-AA, Fractalkine, TGF-α, IL-10, IL-6, IL-1A, IP-10, and IL-8.

In some embodiments, the protein signature involves Ftl-3L, PDGF-AA, Fractalkine, TGF-α, IL-10, IL-6, IL-1A, IP-10, IL-8, and IL-RA. In some embodiments, the protein signature involves GRO, PDGF-AA, Fractalkine, TGF-α, IL-10, IL-6, IL-1A, IP-10, IL-8, and IL-RA. In some embodiments, the protein signature involves GRO, Ftl-3L, Fractalkine, TGF-α, IL-10, IL-6, IL-1A, IP-10, IL-8, and IL-RA. In some embodiments, the protein signature involves GRO, Ftl-3L, PDGF-AA, TGF-α, IL-10, IL-6, IL-1A, IP-10, IL-8, and IL-RA. In some embodiments, the protein signature involves GRO, Ftl-3L, PDGF-AA, Fractalkine, IL-10, IL-6, IL-1A, IP-10, IL-8, and IL-RA. In some embodiments, the protein signature involves GRO, Ftl-3L, PDGF-AA, Fractalkine, TGF-α, IL-6, IL-1A, IP-10, IL-8, and IL-RA. In some embodiments, the protein signature involves GRO, Ftl-3L, PDGF-AA, Fractalkine, TGF-α, IL-10, IL-1A, IP-10, IL-8, and IL-RA. In some embodiments, the protein signature involves GRO, Ftl-3L, PDGF-AA, Fractalkine, TGF-α, IL-10, IL-6, IP-10, IL-8, and IL-RA. In some embodiments, the protein signature involves GRO, Ftl-3L, PDGF-AA, Fractalkine, TGF-α, IL-10, IL-6, IL-1A, IL-8, and IL-RA. In some embodiments, the protein signature involves GRO, Ftl-3L, PDGF-AA, Fractalkine, TGF-α, IL-10, IL-6, IL-1A, IP-10, and IL-RA. In some embodiments, the protein signature involves GRO, Ftl-3L, PDGF-AA, Fractalkine, TGF-α, IL-10, IL-6, IL-1A, IP-10, and IL-8.

In some embodiments, the protein signature involves Ftl-3L, IL-15, Fractalkine, TGF-α, IL-10, IL-6, IL-1A, IP-10, IL-8, and IL-RA. In some embodiments, the protein signature involves GRO, IL-15, Fractalkine, TGF-α, IL-10, IL-6, IL-1A, IP-10, IL-8, and IL-RA. In some embodiments, the protein signature involves GRO, Ftl-3L, Fractalkine, TGF-α, IL-10, IL-6, IL-1A, IP-10, IL-8, and IL-RA. In some embodiments, the protein signature involves GRO, Ftl-3L, IL-15, TGF-α, IL-10, IL-6, IL-1A, IP-10, IL-8, and IL-RA. In some embodiments, the protein signature involves GRO, Ftl-3L, IL-15, Fractalkine, IL-10, IL-6, IL-1A, IP-10, IL-8, and IL-RA. In some embodiments, the protein signature involves GRO, Ftl-3L, IL-15, Fractalkine, TGF-α, IL-6, IL-1A, IP-10, IL-8, and IL-RA. In some embodiments, the protein signature involves GRO, Ftl-3L, IL-15, Fractalkine, TGF-α, IL-10, IL-1A, IP-10, IL-8, and IL-RA. In some embodiments, the protein signature involves GRO, Ftl-3L, IL-15, Fractalkine, TGF-α, IL-10, IL-6, IP-10, IL-8, and IL-RA. In some embodiments, the protein signature involves GRO, Ftl-3L, IL-15, Fractalkine, TGF-α, IL-10, IL-6, IL-1A, IL-8, and IL-RA. In some embodiments, the protein signature involves GRO, Ftl-3L, IL-15, Fractalkine, TGF-α, IL-10, IL-6, IL-1A, IP-10, and IL-RA. In some embodiments, the protein signature involves GRO, Ftl-3L, IL-15, Fractalkine, TGF-α, IL-10, IL-6, IL-1A, IP-10, and IL-8.

In some embodiments, the protein signature involves Ftl-3L, IL-15, PDGF-AA, TGF-α, IL-10, IL-6, IL-1A, IP-10, IL-8, and IL-RA. In some embodiments, the protein signature involves GRO, IL-15, PDGF-AA, TGF-α, IL-10, IL-6, IL-1A, IP-10, IL-8, and IL-RA. In some embodiments, the protein signature involves GRO, Ftl-3L, PDGF-AA, TGF-α, IL-10, IL-6, IL-1A, IP-10, IL-8, and IL-RA. In some embodiments, the protein signature involves GRO, Ftl-3L, IL-15, TGF-α, IL-10, IL-6, IL-1A, IP-10, IL-8, and IL-RA. In some embodiments, the protein signature involves GRO, Ftl-3L, IL-15, PDGF-AA, IL-10, IL-6, IL-1A, IP-10, IL-8, and IL-RA. In some embodiments, the protein signature involves GRO, Ftl-3L, IL-15, PDGF-AA, TGF-α, IL-6, IL-1A, IP-10, IL-8, and IL-RA. In some embodiments, the protein signature involves GRO, Ftl-3L, IL-15, PDGF-AA, TGF-α, IL-10, IL-1A, IP-10, IL-8, and IL-RA. In some embodiments, the protein signature involves GRO, Ftl-3L, IL-15, PDGF-AA, TGF-α, IL-10, IL-6, IP-10, IL-8, and IL-RA. In some embodiments, the protein signature involves GRO, Ftl-3L, IL-15, PDGF-AA, TGF-α, IL-10, IL-6, IL-1A, IL-8, and IL-RA. In some embodiments, the protein signature involves GRO, Ftl-3L, IL-15, PDGF-AA, TGF-α, IL-10, IL-6, IL-1A, IP-10, and IL-RA. In some embodiments, the protein signature involves GRO, Ftl-3L, IL-15, PDGF-AA, TGF-α, IL-10, IL-6, IL-1A, IP-10, and IL-8.

In some embodiments, the protein signature involves Ftl-3L, IL-15, PDGF-AA, Fractalkine, IL-10, IL-6, IL-1A, IP-10, IL-8, and IL-RA. In some embodiments, the protein signature involves GRO, IL-15, PDGF-AA, Fractalkine, IL-10, IL-6, IL-1A, IP-10, IL-8, and IL-RA. In some embodiments, the protein signature involves GRO, Ftl-3L, PDGF-AA, Fractalkine, IL-10, IL-6, IL-1A, IP-10, IL-8, and IL-RA. In some embodiments, the protein signature involves GRO, Ftl-3L, IL-15, Fractalkine, IL-10, IL-6, IL-1A, IP-10, IL-8, and IL-RA. In some embodiments, the protein signature involves GRO, Ftl-3L, IL-15, PDGF-AA, IL-10, IL-6, IL-1A, IP-10, IL-8, and IL-RA. In some embodiments, the protein signature involves GRO, Ftl-3L, IL-15, PDGF-AA, Fractalkine, IL-6, IL-1A, IP-10, IL-8, and IL-RA. In some embodiments, the protein signature involves GRO, Ftl-3L, IL-15, PDGF-AA, Fractalkine, IL-10, IL-1A, IP-10, IL-8, and IL-RA. In some embodiments, the protein signature involves GRO, Ftl-3L, IL-15, PDGF-AA, Fractalkine, IL-10, IL-6, IP-10, IL-8, and IL-RA. In some embodiments, the protein signature involves GRO, Ftl-3L, IL-15, PDGF-AA, Fractalkine, IL-10, IL-6, IL-1A, IL-8, and IL-RA. In some embodiments, the protein signature involves GRO, Ftl-3L, IL-15, PDGF-AA, Fractalkine, IL-10, IL-6, IL-1A, IP-10, and IL-RA. In some embodiments, the protein signature involves GRO, Ftl-3L, IL-15, PDGF-AA, Fractalkine, IL-10, IL-6, IL-1A, IP-10, and IL-8.

In some embodiments, the protein signature involves Ftl-3L, IL-15, PDGF-AA, Fractalkine, TGF-α, IL-6, IL-1A, IP-10, IL-8, and IL-RA. In some embodiments, the protein signature involves GRO, IL-15, PDGF-AA, Fractalkine, TGF-α, IL-6, IL-1A, IP-10, IL-8, and IL-RA. In some embodiments, the protein signature involves GRO, Ftl-3L, PDGF-AA, Fractalkine, TGF-α, IL-6, IL-1A, IP-10, IL-8, and IL-RA. In some embodiments, the protein signature involves GRO, Ftl-3L, IL-15, Fractalkine, TGF-α, IL-6, IL-1A, IP-10, IL-8, and IL-RA. In some embodiments, the protein signature involves GRO, Ftl-3L, IL-15, PDGF-AA, TGF-α, IL-6, IL-1A, IP-10, IL-8, and IL-RA. In some embodiments, the protein signature involves GRO, Ftl-3L, IL-15, PDGF-AA, Fractalkine, IL-6, IL-1A, IP-10, IL-8, and IL-RA. In some embodiments, the protein signature involves GRO, Ftl-3L, IL-15, PDGF-AA, Fractalkine, TGF-α, IL-1A, IP-10, IL-8, and IL-RA. In some embodiments, the protein signature involves GRO, Ftl-3L, IL-15, PDGF-AA, Fractalkine, TGF-α, IL-6, IP-10, IL-8, and IL-RA. In some embodiments, the protein signature involves GRO, Ftl-3L, IL-15, PDGF-AA, Fractalkine, TGF-α, IL-6, IL-1A, IL-8, and IL-RA. In some embodiments, the protein signature involves GRO, Ftl-3L, IL-15, PDGF-AA, Fractalkine, TGF-α, IL-6, IL-1A, IP-10, and IL-RA. In some embodiments, the protein signature involves GRO, Ftl-3L, IL-15, PDGF-AA, Fractalkine, TGF-α, IL-6, IL-1A, IP-10, and IL-8.

In some embodiments, the protein signature involves Ftl-3L, IL-15, PDGF-AA, Fractalkine, TGF-α, IL-10, IL-1A, IP-10, IL-8, and IL-RA. In some embodiments, the protein signature involves GRO, IL-15, PDGF-AA, Fractalkine, TGF-α, IL-10, IL-1A, IP-10, IL-8, and IL-RA. In some embodiments, the protein signature involves GRO, Ftl-3L, PDGF-AA, Fractalkine, TGF-α, IL-10, IL-1A, IP-10, IL-8, and IL-RA. In some embodiments, the protein signature involves GRO, Ftl-3L, IL-15, Fractalkine, TGF-α, IL-10, IL-1A, IP-10, IL-8, and IL-RA. In some embodiments, the protein signature involves GRO, Ftl-3L, IL-15, PDGF-AA, TGF-α, IL-10, IL-1A, IP-10, IL-8, and IL-RA. In some embodiments, the protein signature involves GRO, Ftl-3L, IL-15, PDGF-AA, Fractalkine, IL-10, IL-1A, IP-10, IL-8, and IL-RA. In some embodiments, the protein signature involves GRO, Ftl-3L, IL-15, PDGF-AA, Fractalkine, TGF-α, IL-1A, IP-10, IL-8, and IL-RA. In some embodiments, the protein signature involves GRO, Ftl-3L, IL-15, PDGF-AA, Fractalkine, TGF-α, IL-10, IP-10, IL-8, and IL-RA. In some embodiments, the protein signature involves GRO, Ftl-3L, IL-15, PDGF-AA, Fractalkine, TGF-α, IL-10, IL-1A, IL-8, and IL-RA. In some embodiments, the protein signature involves GRO, Ftl-3L, IL-15, PDGF-AA, Fractalkine, TGF-α, IL-10, IL-1A, IP-10, and IL-RA. In some embodiments, the protein signature involves GRO, Ftl-3L, IL-15, PDGF-AA, Fractalkine, TGF-α, IL-10, IL-1A, IP-10, and IL-8.

In some embodiments, the protein signature involves Ftl-3L, IL-15, PDGF-AA, Fractalkine, TGF-α, IL-10, IL-6, IP-10, IL-8, and IL-RA. In some embodiments, the protein signature involves GRO, IL-15, PDGF-AA, Fractalkine, TGF-α, IL-10, IL-6, IP-10, IL-8, and IL-RA. In some embodiments, the protein signature involves GRO, Ftl-3L, PDGF-AA, Fractalkine, TGF-α, IL-10, IL-6, IP-10, IL-8, and IL-RA. In some embodiments, the protein signature involves GRO, Ftl-3L, IL-15, Fractalkine, TGF-α, IL-10, IL-6, IP-10, IL-8, and IL-RA. In some embodiments, the protein signature involves GRO, Ftl-3L, IL-15, PDGF-AA, TGF-α, IL-10, IL-6, IP-10, IL-8, and IL-RA. In some embodiments, the protein signature involves GRO, Ftl-3L, IL-15, PDGF-AA, Fractalkine, IL-10, IL-6, IP-10, IL-8, and IL-RA. In some embodiments, the protein signature involves GRO, Ftl-3L, IL-15, PDGF-AA, Fractalkine, TGF-α, IL-6, IP-10, IL-8, and IL-RA. In some embodiments, the protein signature involves GRO, Ftl-3L, IL-15, PDGF-AA, Fractalkine, TGF-α, IL-10, IP-10, IL-8, and IL-RA. In some embodiments, the protein signature involves GRO, Ftl-3L, IL-15, PDGF-AA, Fractalkine, TGF-α, IL-10, IL-6, IL-8, and IL-RA. In some embodiments, the protein signature involves GRO, Ftl-3L, IL-15, PDGF-AA, Fractalkine, TGF-α, IL-10, IL-6, IP-10, and IL-RA. In some embodiments, the protein signature involves GRO, Ftl-3L, IL-15, PDGF-AA, Fractalkine, TGF-α, IL-10, IL-6, IP-10, and IL-8.

In some embodiments, the protein signature involves Ftl-3L, IL-15, PDGF-AA, Fractalkine, TGF-α, IL-10, IL-6, IL-1A, IL-8, and IL-RA. In some embodiments, the protein signature involves GRO, IL-15, PDGF-AA, Fractalkine, TGF-α, IL-10, IL-6, IL-1A, IL-8, and IL-RA. In some embodiments, the protein signature involves GRO, Ftl-3L, PDGF-AA, Fractalkine, TGF-α, IL-10, IL-6, IL-1A, IL-8, and IL-RA. In some embodiments, the protein signature involves GRO, Ftl-3L, IL-15, Fractalkine, TGF-α, IL-10, IL-6, IL-1A, IL-8, and IL-RA. In some embodiments, the protein signature involves GRO, Ftl-3L, IL-15, PDGF-AA, TGF-α, IL-10, IL-6, IL-1A, IL-8, and IL-RA. In some embodiments, the protein signature involves GRO, Ftl-3L, IL-15, PDGF-AA, Fractalkine, IL-10, IL-6, IL-1A, IL-8, and IL-RA. In some embodiments, the protein signature involves GRO, Ftl-3L, IL-15, PDGF-AA, Fractalkine, TGF-α, IL-6, IL-1A, IL-8, and IL-RA. In some embodiments, the protein signature involves GRO, Ftl-3L, IL-15, PDGF-AA, Fractalkine, TGF-α, IL-10, IL-1A, IL-8, and IL-RA. In some embodiments, the protein signature involves GRO, Ftl-3L, IL-15, PDGF-AA, Fractalkine, TGF-α, IL-10, IL-6, IL-8, and IL-RA. In some embodiments, the protein signature involves GRO, Ftl-3L, IL-15, PDGF-AA, Fractalkine, TGF-α, IL-10, IL-6, IL-1A, and IL-RA. In some embodiments, the protein signature involves GRO, Ftl-3L, IL-15, PDGF-AA, Fractalkine, TGF-α, IL-10, IL-6, IL-1A, and IL-8.

In some embodiments, the protein signature involves Ftl-3L, IL-15, PDGF-AA, Fractalkine, TGF-α, IL-10, IL-6, IL-1A, IP-10, and IL-RA. In some embodiments, the protein signature involves GRO, IL-15, PDGF-AA, Fractalkine, TGF-α, IL-10, IL-6, IL-1A, IP-10, and IL-RA. In some embodiments, the protein signature involves GRO, Ftl-3L, PDGF-AA, Fractalkine, TGF-α, IL-10, IL-6, IL-1A, IP-10, and IL-RA. In some embodiments, the protein signature involves GRO, Ftl-3L, IL-15, Fractalkine, TGF-α, IL-10, IL-6, IL-1A, IP-10, and IL-RA. In some embodiments, the protein signature involves GRO, Ftl-3L, IL-15, PDGF-AA, TGF-α, IL-10, IL-6, IL-1A, IP-10, and IL-RA. In some embodiments, the protein signature involves GRO, Ftl-3L, IL-15, PDGF-AA, Fractalkine, IL-10, IL-6, IL-1A, IP-10, and IL-RA. In some embodiments, the protein signature involves GRO, Ftl-3L, IL-15, PDGF-AA, Fractalkine, TGF-α, IL-6, IL-1A, IP-10, and IL-RA. In some embodiments, the protein signature involves GRO, Ftl-3L, IL-15, PDGF-AA, Fractalkine, TGF-α, IL-10, IL-1A, IP-10, and IL-RA. In some embodiments, the protein signature involves GRO, Ftl-3L, IL-15, PDGF-AA, Fractalkine, TGF-α, IL-10, IL-6, IP-10, and IL-RA. In some embodiments, the protein signature involves GRO, Ftl-3L, IL-15, PDGF-AA, Fractalkine, TGF-α, IL-10, IL-6, IL-1A, and IL-RA. In some embodiments, the protein signature involves GRO, Ftl-3L, IL-15, PDGF-AA, Fractalkine, TGF-α, IL-10, IL-6, IL-1A, and IP-10.

In some embodiments, the protein signature involves Ftl-3L, IL-15, PDGF-AA, Fractalkine, TGF-α, IL-10, IL-6, IL-1A, IP-10, and IL-8. In some embodiments, the protein signature involves GRO, IL-15, PDGF-AA, Fractalkine, TGF-α, IL-10, IL-6, IL-1A, IP-10, and IL-8. In some embodiments, the protein signature involves GRO, Ftl-3L, PDGF-AA, Fractalkine, TGF-α, IL-10, IL-6, IL-1A, IP-10, and IL-8. In some embodiments, the protein signature involves GRO, Ftl-3L, IL-15, Fractalkine, TGF-α, IL-10, IL-6, IL-1A, IP-10, and IL-8. In some embodiments, the protein signature involves GRO, Ftl-3L, IL-15, PDGF-AA, TGF-α, IL-10, IL-6, IL-1A, IP-10, and IL-8. In some embodiments, the protein signature involves GRO, Ftl-3L, IL-15, PDGF-AA, Fractalkine, IL-10, IL-6, IL-1A, IP-10, and IL-8. In some embodiments, the protein signature involves GRO, Ftl-3L, IL-15, PDGF-AA, Fractalkine, TGF-α, IL-6, IL-1A, IP-10, and IL-8. In some embodiments, the protein signature involves GRO, Ftl-3L, IL-15, PDGF-AA, Fractalkine, TGF-α, IL-10, IL-1A, IP-10, and IL-8. In some embodiments, the protein signature involves GRO, Ftl-3L, IL-15, PDGF-AA, Fractalkine, TGF-α, IL-10, IL-6, IP-10, and IL-8. In some embodiments, the protein signature involves GRO, Ftl-3L, IL-15, PDGF-AA, Fractalkine, TGF-α, IL-10, IL-6, IL-1A, and IL-8. In some embodiments, the protein signature involves GRO, Ftl-3L, IL-15, PDGF-AA, Fractalkine, TGF-α, IL-10, IL-6, IL-1A, and IP-10.

In some embodiments, the protein signature involves at least GRO, IL-1RA, or a combination thereof. In some embodiments, the protein signature involves GRO and Flt-3L. In some embodiments, the protein signature involves GRO, Ftl-3L, IL-15, PDGF-AA, IL-6, IL-1A, IP-10, IL-8, and IL-RA. In some embodiments, the protein signature involves GRO, Ftl-3L, IL-15, IL-1A, IP-10, IL-8, and IL-RA. In some embodiments, the protein signature involves GRO, Ftl-3L, IP-10, IL-8, and IL-RA. In some embodiments, the protein signature involves IL-RA and TGF-α. In some embodiments, the protein signature involves IL-RA, IL-15, and TGF-α. In some embodiments, the protein signature involves IL-RA and Eotaxin.

In some embodiments, the method involves assaying a tumor microenvironment sample from the subject for one or more of these proteins. Techniques for measuring protein levels are known and include immunoassays. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Survival and Risk Score

A survival or risk score can be determined using standard statistical methods, such as multivariate analysis. In some embodiments, the risk score is a regression value. For example, the differential expression may be analyzed by multivariate regression analysis (e.g., determined by linear regression) or principal component analysis to derive a risk score. In other embodiments, specific soluble immune proteins are used to calculate the risk score. For example, in some embodiments, levels of Eotaxin, FGF-2, IL-4, IP-10, and TNFα relative to control values are positively correlated to survival score; and levels of G-CSF and PDGF-AA relative to control values are negatively correlated to survival score.

In some implementations of the method, the regression function is one of: linear regression, a broken linear regression, a logistic regression, a polynomial regression, a ridge regression, or a lasso regression.

In some embodiments, the disclosed methods involve numerous data points that are best managed and stored in a computer readable form. Therefore, in some embodiments, the survival score is a regression value derived from the protein expression levels as a weighted function of the quantified levels. The weighted function can be derived from linear regression analysis of experimental results comparing detected protein expression levels to that of subjects with poor and prolonged post-surgical survival. Each protein level can be multiplied by a weighting constant and summed.

Prior to analysis, the data in each dataset can be collected by measuring the values for each soluble immune protein, usually in duplicate or triplicate or in multiple replicates. The data may be manipulated, for example raw data may be transformed using standard curves, and the average of replicate measurements used to calculate the average and standard deviation for each patient. These values may be transformed before being used in the models, e.g. log-transformed, Box-Cox transformed, etc. This data can then be input into an analytical process with defined parameter.

The analytic classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm.

Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2, 3, 4, 5, 6, or 7. In one embodiment, the number of features that may be used by an analytical process to classify a test subject is optimized to allow a classification of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. Such algorithms classify complex spectra from biological materials, such as a blood sample, to distinguish subjects as normal or as possessing biomarker levels characteristic of a particular condition. In other embodiments, a data analysis algorithm of the disclosure comprises ANOVA and nonparametric equivalents, linear discriminant analysis, logistic regression analysis, nearest neighbor classifier analysis, neural networks, principal component analysis, hierarchical cluster analysis, quadratic discriminant analysis, regression classifiers and support vector machines.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

Therapy Selection

The disclosed protein signatures can be used to select a suitable therapy for a subject with PDAC. In some embodiments, the subject is determined to have a good post-surgical survival score. In these embodiments, the subject can be treated by surgical resection of the tumor. A pancreatectomy is the surgical removal of all or part of the pancreas. Several types of pancreatectomy exist, including pancreaticoduodenectomy (Whipple procedure), distal pancreatectomy, segmental pancreatectomy, and total pancreatectomy.

In some embodiments, the subject is determined to have a poor post-surgical survival score. In these embodiments, the subject can be treated with palliative care to improve quality of life. In some cases, these subjects are treated with a chemotherapy, such as gemcitabine.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Methods

Sample Collection

The study was approved by the Institutional Review Board at the University of Florida. Informed consent was obtained from all study participants. A prospectively maintained database of all patients undergoing surgical pancreatic resection was maintained. Consecutive patients undergoing a pancreatectomy for PDAC were included. Patients that received neoadjuvant therapy were clinically staged by multidisciplinary tumor board review of imaging as borderline resectable as defined by NCCN criteria. Patients were censored at last contact with our surgical team either by hospital stay, clinic visit, or phone call.

At the time of surgical resection, a small piece of tumor was excised before the surgical specimen was sent for histopathologic processing. This specimen was subsequently divided into pieces for histologic assessment (formalin fixed) and for protein analysis (snap frozen in liquid nitrogen).

Soluble Protein Analysis

Tissues were dissociated mechanically and homogenized in lysis buffer containing protease inhibitors as previously described (Delitto D, et al. BMC Cancer. 2015 15:783). Briefly, the homogenates were centrifuged at 12,000×g for 15 min at 4° C. to separate insoluble debris from the supernatant Total protein concentrations of each supernatant were determined using a protein quantification kit (Bio-Rad, Hercules, CA, USA). The supernatants were analyzed by Milliplex Premixed 36-Plex Immunology Multiplex Assays (Millipore, Merk KGaA, Darmstadt, Germany) according to the manufacturer's protocol. The final values are expressed as [pg of cytokine]/[mg of total protein].

Statistical Analysis

The primary endpoint was overall survival defined as time from surgical resection to death or last-follow up. Analyte distributions were highly skewed and thus were first log-transformed. A Cox proportional hazards regression was applied to model overall survival reporting both the raw p value with an adjustment for false discovery (Benjamini Y H, et al. Journal of the Royal Statistical Society Series B (Methodological). 1995; 57(1):289-300). For the panel of Luminex analytes, protein levels were natural log transformed and scaled to have mean zero and standard deviation of one. Penalized log partial likelihood methods were then applied (Tibshirani R. Stat Med. 1997 16(4):385-95) to select a subset of analytes and to derive shrunken regression coefficients. The penalized and shrunken regression estimates are less likely to result in model overfitting. The shrinkage tuning factor was selected using leave-one out cross-validation of the likelihood function. Using the resulting penalized regression coefficients, a mortality risk score termed "Protein Risk Score" was computed. Regression models were checked for linearity, interactions, and validity of the proportional hazards assumptions. Statistical analysis used the R packages rms (Benjamini Y H, et al. Journal of the Royal Statistical Society Series B (Methodological). 1995; 57(1):289-300) and penalized (Tibshirani R. Stat Med. 1997 16(4):385-95).

Results

Patient and Sample Data

Tissue samples were collected from 36 consecutive patients receiving a pancreatectomy for PDAC. Patient clinical parameters are shown in Table 1. A single patient was lost to follow up at 11.7 months post operatively. At the time of data collection (Feb. 21, 2018), six patients remain alive with last follow-up at 12, 46, 49, 49, 58, and 76 months (median=49 months). The 36 patient cohort had a median overall survival (OS) of 12 months (95% CI=7-21 months). Four patients died within 2 months of surgery, however, based on a hierarchical agglomeration cluster analysis, their analyte profile could not be distinguished from the remaining 32 patients. Therefore, the primary analysis of analyte-associated prognosis included all 36 patients.

Analyte Associations

A single analyte, EGF, was removed from the study as concentrations of this protein were below detection levels of the assay in 29 of the tissue samples. The remaining 35 analytes were individually log-transformed and tested for association with overall survival. FIG. 1 shows hierarchical clustering of the analytes with 26 having a positive association with overall survival and 9 having a negative association with overall survival. Analytes were then tested for association with overall survival by Cox proportional hazards regression. Five analytes were significant with p-value<0.05. However, when adjusted for multiple comparisons, the smallest expected false discovery rate was 25.3%. Therefore, no single analyte was found to be significantly associated with overall survival in this cohort. Table 2 displays the top ten analytes ranked by p value.

Clinical/Pathologic Associations

Among a panel of patient clinical parameters, five were associated with survival: number of positive lymph nodes, positive lymph node ratio (number of positive nodes divided by total number of nodes collected), R1 positive margin status (cancer cells within 1 mm of the surgical margin), operation performed, and portal vein resection (Table 4). No pre-operative information, age, sex, CA19-9, or neoadjuvant therapy, was found to be significantly associated with overall survival.

Prognostic Modeling

Figure 6:
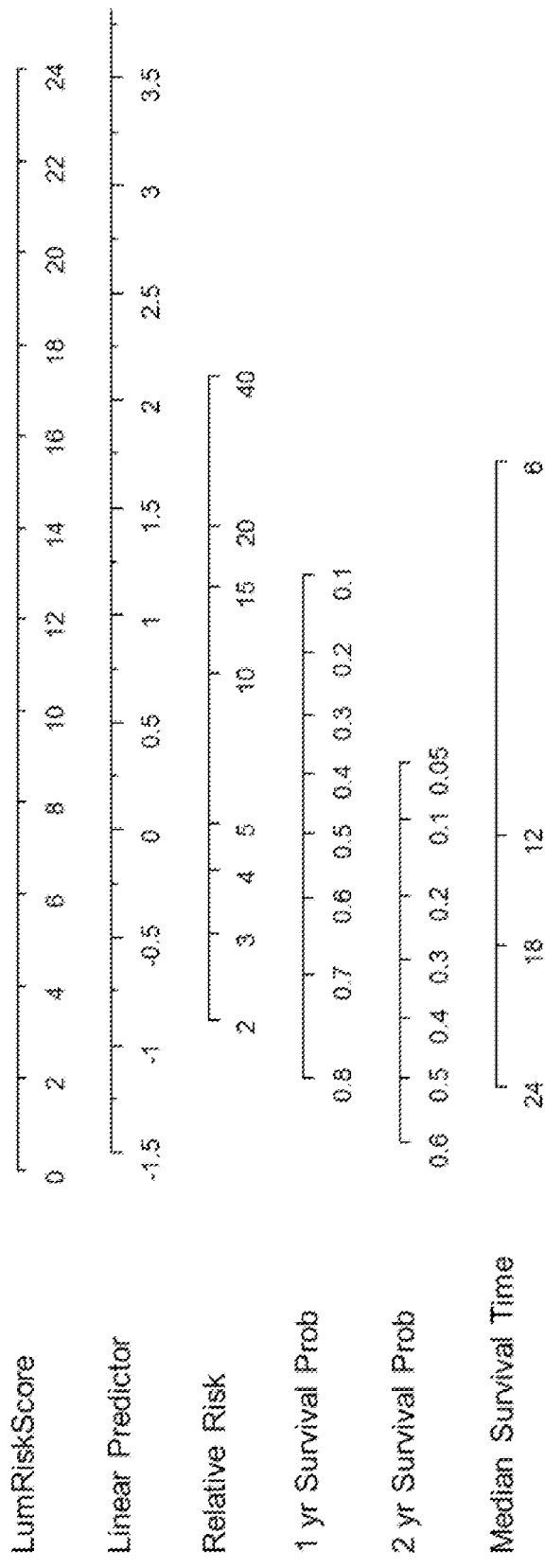
FIG. 6 is a Protein Risk Score predictive nomogram for overall survival.
Figure 7:
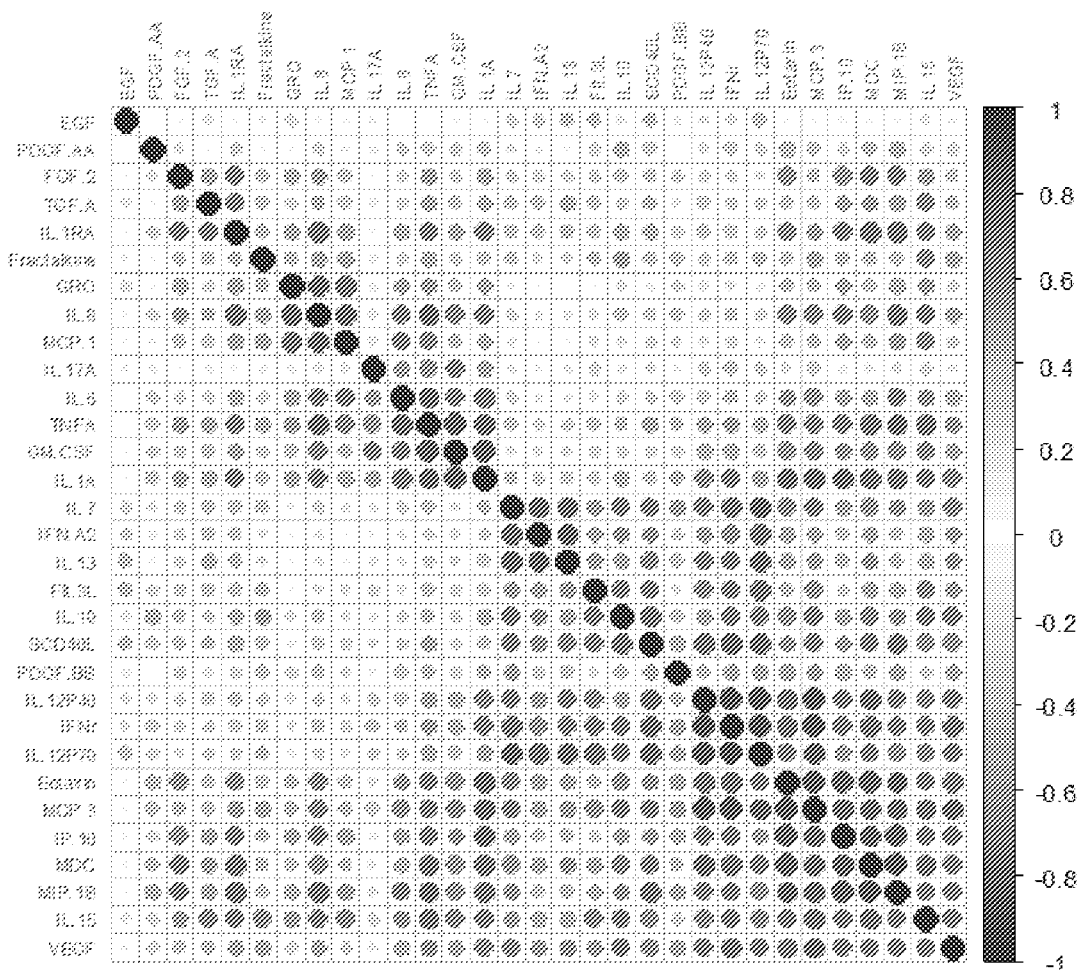
FIG. 7 is a Spearman correlation matrix with the order of presentation by clustering. The blocks of dark blue dots (positive correlation) on the diagonal "travel together". PDGF.AA is negatively correlated or uncorrelated with nearly everything.

The penalization and shrinkage log partial likelihood method was applied to the analytes. Using a leave-one out cross-validation of the 36 samples, the final tuning factor was optimized giving us eight non-zero coefficients (Table 3). A prognostic model was then constructed using the penalized regression coefficients creating a linear combination of the eight-analyte signature to calculate predicted relative risk for each patient $f(x)=a$ (FGF-2)+b (Eotaxin)+c (G-CSF)+d (GM-CSF)+e (IL-13)+g (IL-4)+h (IP-10)+i (RANTES). This relative risk was multiplied by 1000 and labeled "Protein Risk Score". Other known pre-operative factors including age, sex, Ca19-9 levels, and neoadjuvant therapy did not contribute significantly to explaining variation in survival and were not included as covariates in the model. FIG. 6 depicts an overall survival nomogram using the Protein Risk Score for model-based probabilities of 1 and 2 year survival as well as predicted median survival.

Figure 2:
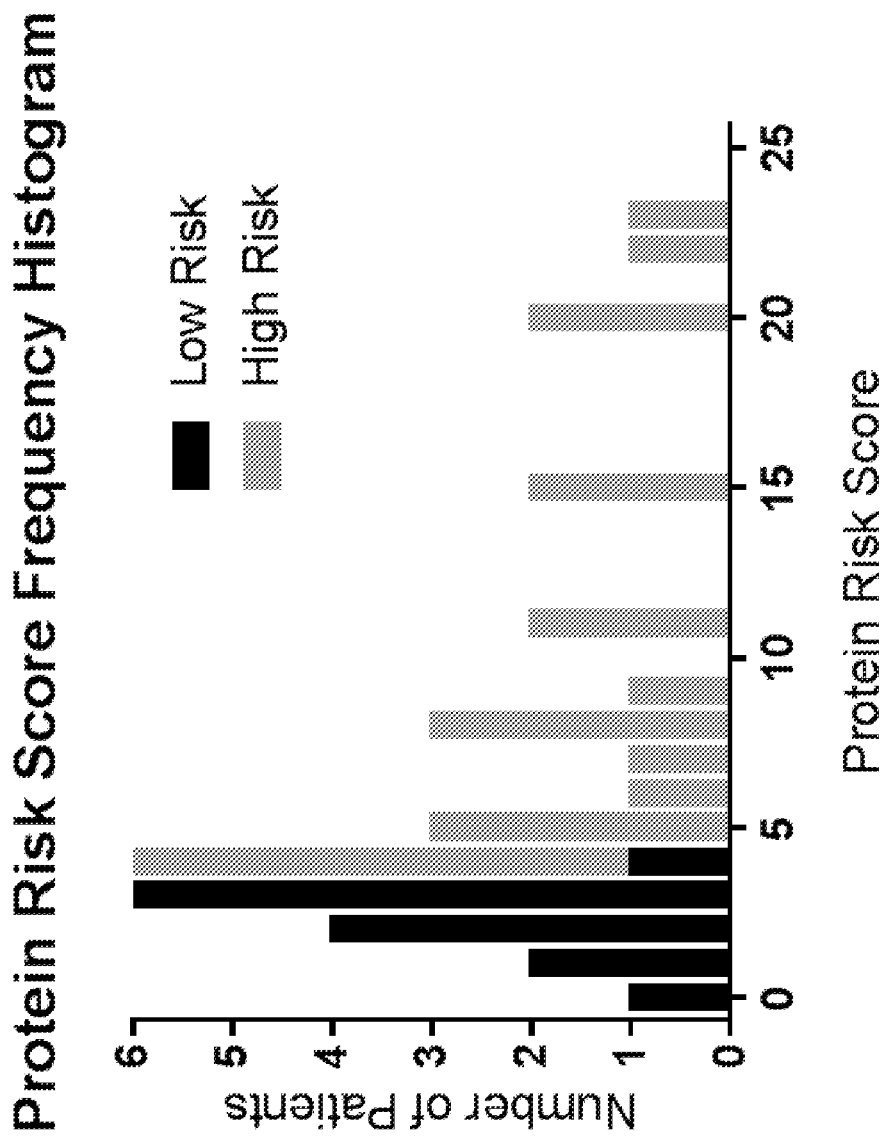
FIG. 2 shows frequency histogram of the Protein Risk Scores. All 36 Protein Risk Scores were calculated and plotted on the histogram. The median risk score (4.8) separates the cohort into two groups. Scores above the median are designated high risk (gray) and scores below the median designated low risk (black).
Figure 3A:
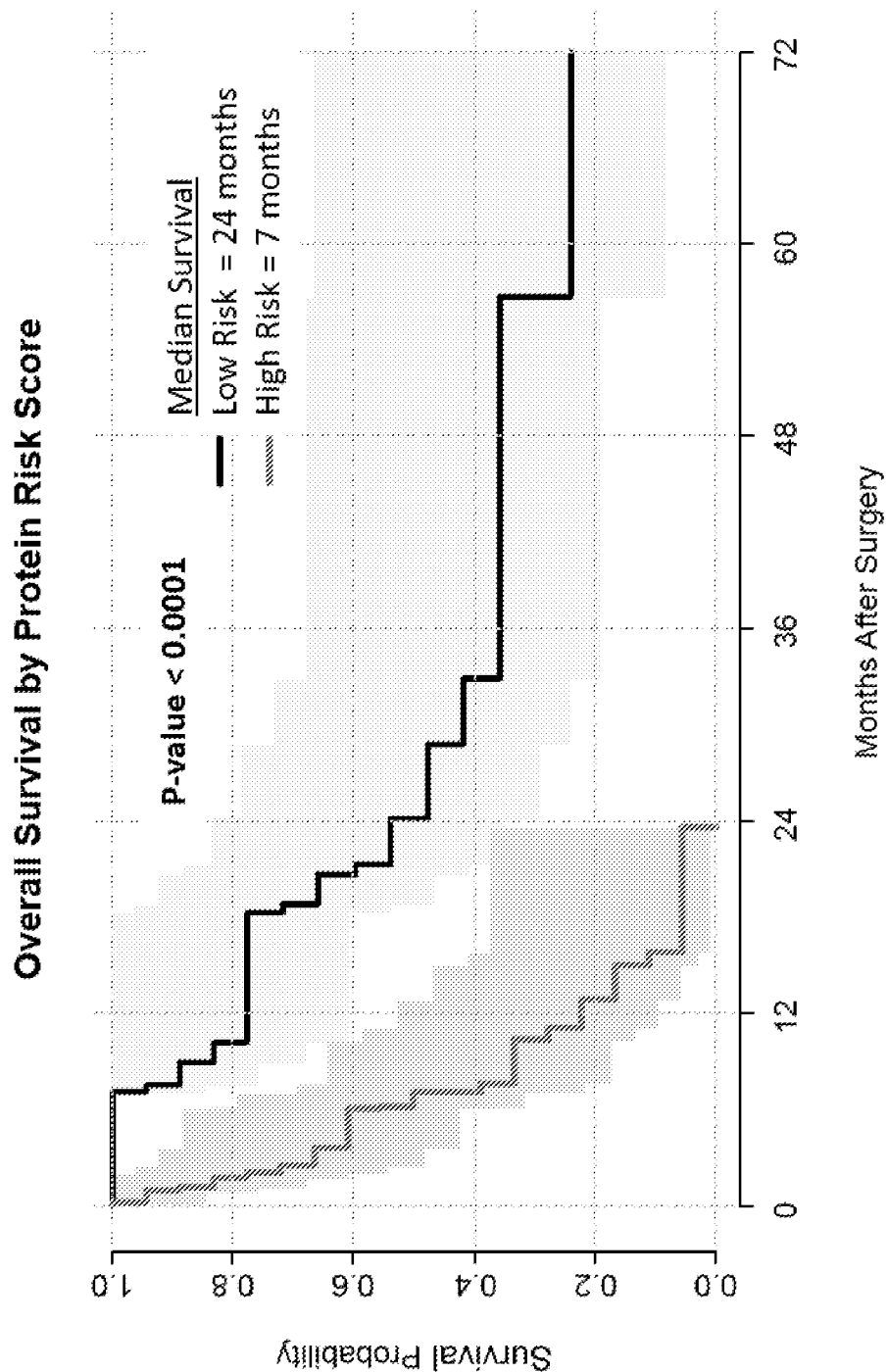
FIGS. 3A and 3B are Kaplan-Meier survival curves for Protein Risk Scores.
Figure 3B:
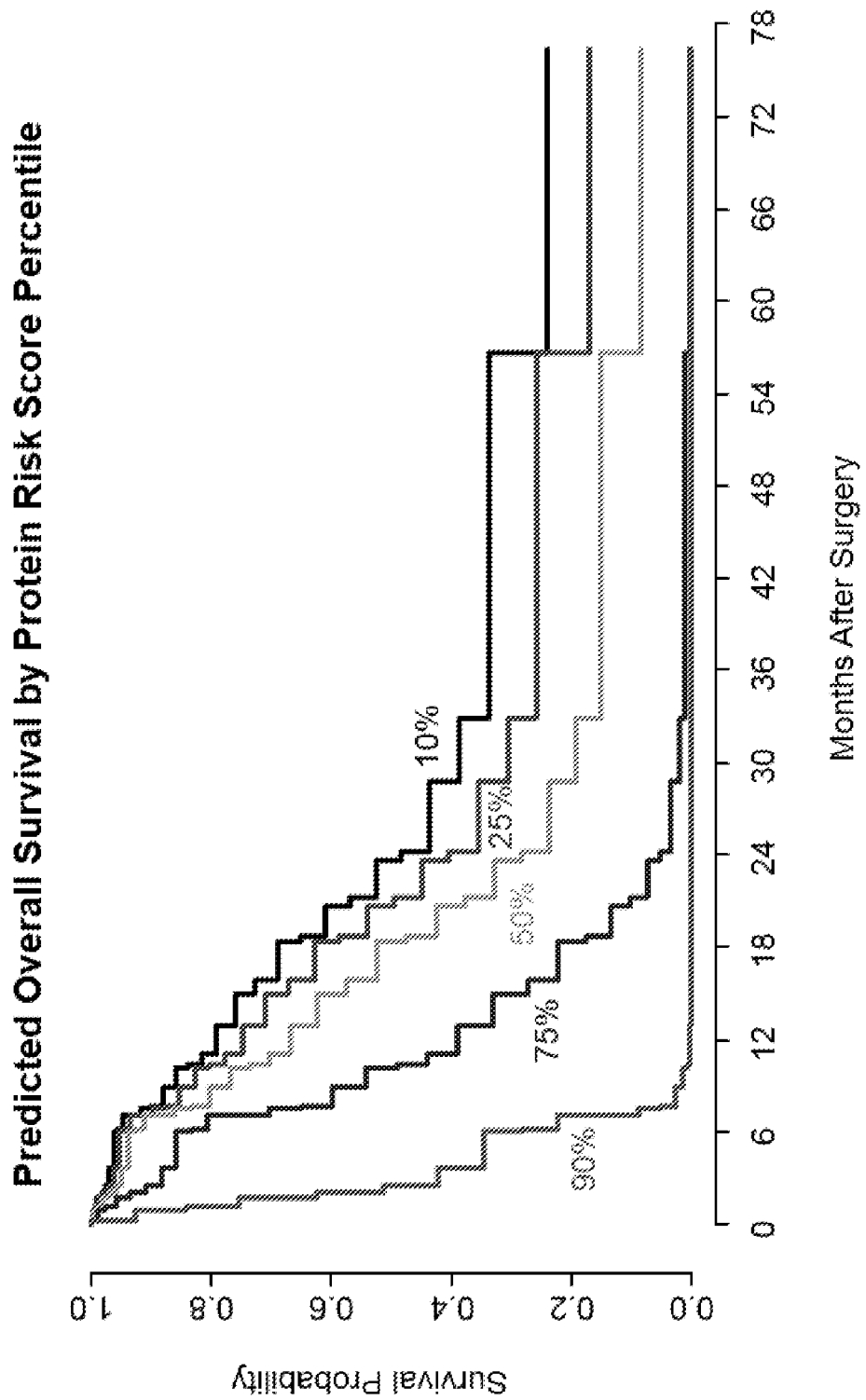

FIG. 2 demonstrates a frequency histogram of the 36 samples' Protein Risk Scores. The scores were divided at the median into low risk (<4.8) and high risk (>4.8) groups with 18 samples in each. No pre-operative factors were different between high risk and lows risk groups (Table 5). The positive lymph node ratio was the only post-operative factor that differed between the high and low risk groups (median 0.225 vs 0.088; p=0.026). The Kaplan-Meier survival curves were plotted in FIG. 3A and found to be significantly different (P<0.001) with the high risk group having a median survival of 7 months while the low risk group had a median survival of 24 months. In the high risk group, no patients survived beyond 24 months and only 4 patients (22%) survived beyond 12 months. In the low risk group, 14 (78%) patients survived at least 12 months and 9 (50%) survived beyond 24 months. FIG. 3B displays the Kaplan-Meier predicted overall survival curves for several different percentiles of the Protein Risk Score. In the $90^{th}$ percentile of the risk score, the curves reveals almost no predicted survival beyond 12 months, and in the $75^{th}$ percentile, shows a less than 0.4 survival probability at 12 months as well as a less than 0.05 survival probability at 24 months. Both the $25^{th}$ and $10^{th}$ percentiles have a nearly 0.8 survival probability at 12 months with a 0.4 and 0.5 survival probably by 24 months. These survival probabilities suggest a high Protein Risk Score is specific for patients that will have poor post-surgical survival, but not necessarily sensitive for all those with a poor post-surgical survival.

In the cohort, only 1 (6%) patient of the 18 in the high risk group lived more than 15 month national median survival after surgery (Siegel R L, et al. C A Cancer J Clin. 2016 66(1):7-30). The low risk group had 3 patients (16.7%) that lived less than this 15 month milestone. This means the prognostic model's overall accuracy on our patient cohort was 32 out of 36 (89%) in determining if the high risk patients would live less than the national median survival after surgery and if the low risk patients would live longer than the 15 month national median survival.

Figure 4A:
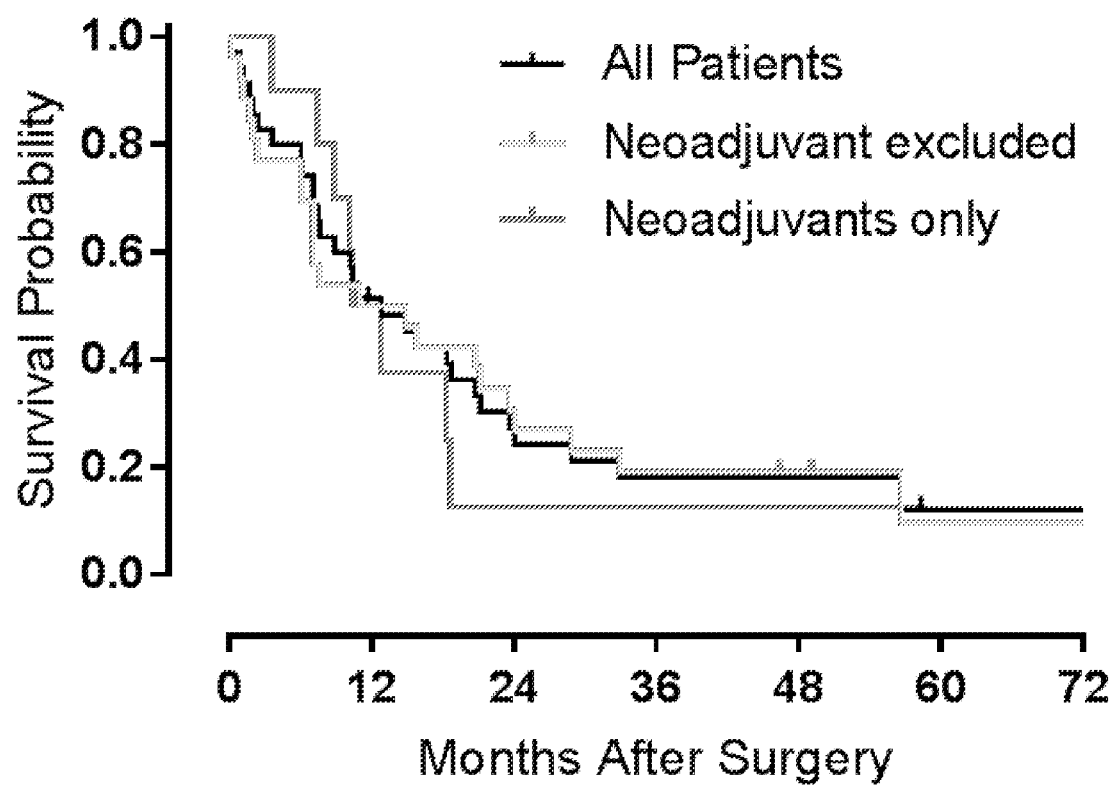
FIGS. 4A and 4B are survival curves of patients with and without neoadjuvant therapy.
Figure 4B:
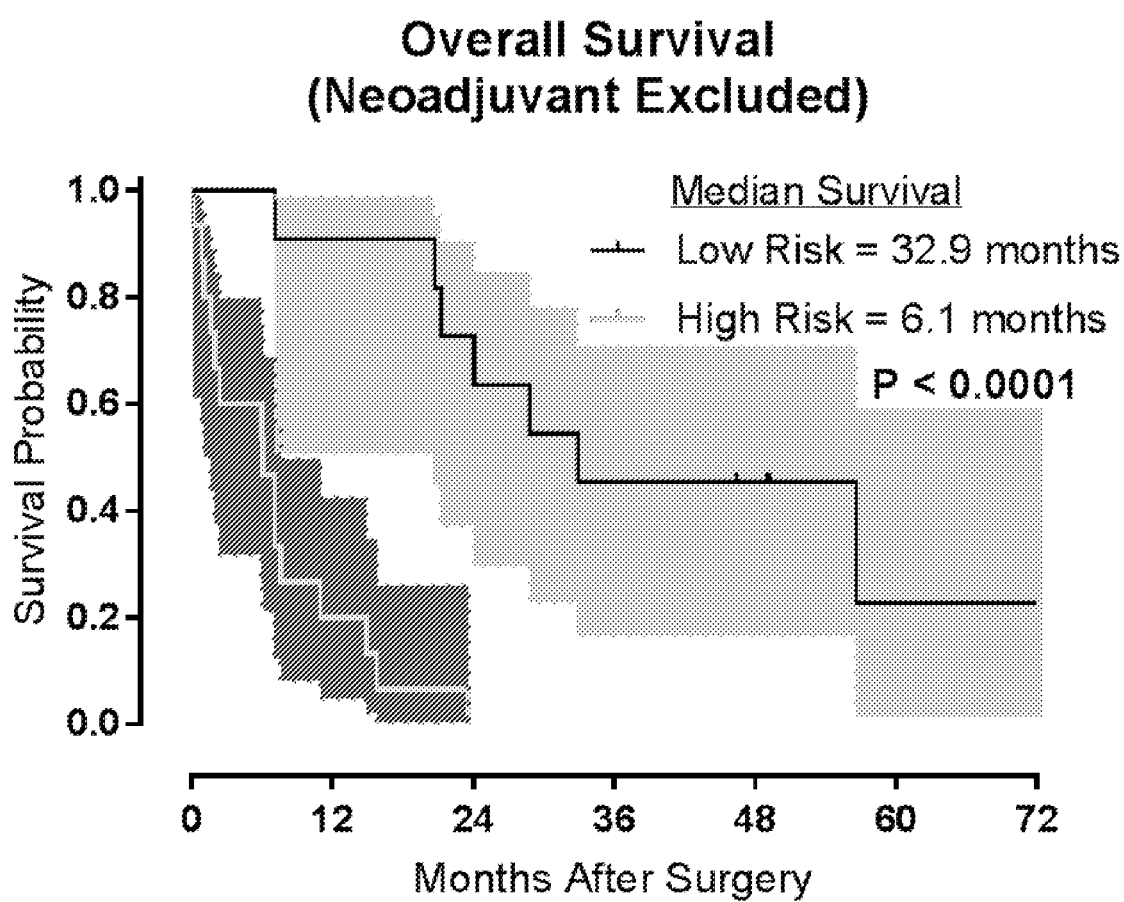

Also explored was whether patients receiving neoadjuvant therapy might have altered the tumor microenvironment impacting the Protein Risk Score. On univariate analysis (Table 4), receipt of neoadjuvant therapy was not associated with overall survival. FIG. 4A displays the survival curves for all patients, patients that had no neoadjuvant treatment, and patients that had neoadjuvant treatment. Survival for patients receiving neoadjuvant treatment did not significantly differ from those who did not receive neoadjuvant treatment with overall survival in therapy naïve patients of 13 months versus 11 months for patients who received neoadjuvant therapy (p=0.585). The number of patients who received neoadjuvant therapy was not different between low risk and high risk groups (Table 5), but it may have altered the survival between the groups. As seen in FIG. 4B, if the neoadjuvant patients are removed from the low risk (n=7) and the high risk (n=3) groups, the overall survival remains significantly longer in the low risk compare to the high risk with median survival times of 32.9 months and 6.1 months, respectively (p<0.0001). This suggests neoadjuvant therapy does not promote an increase in survival time for the low risk group and that our prognostic model may be applied to both patients who have and have not received neoadjuvant therapy.

Figure 5A:
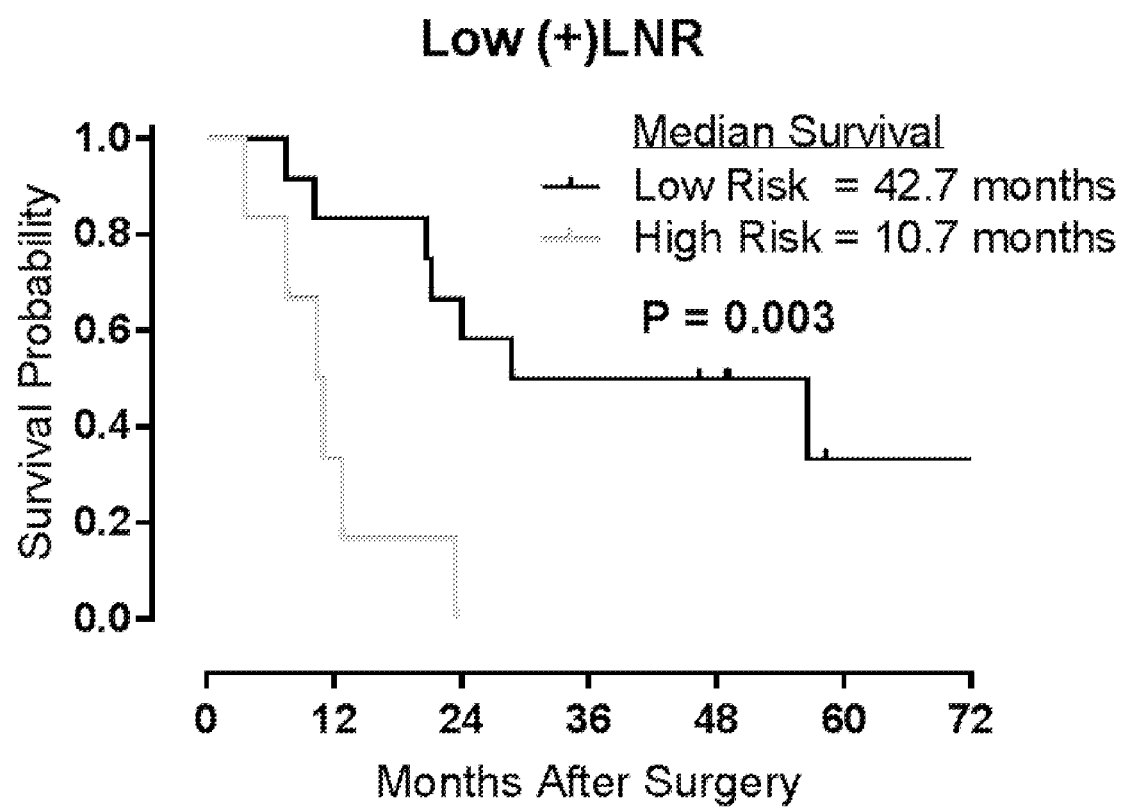
FIGS. 5A and 5B are survival curves of patients with high and low positive LNRs. For patients with a low positive LNR, the high risk Protein Scores are significantly different from the low risk Protein Scores (FIG. 5A). For patients with a high positive LNR, the high risk Protein Scores are significantly different from the low risk Protein Scores (FIG. 5B). All p-values calculated using the log-rank test. LNR lymph node ratio.
Figure 5B:
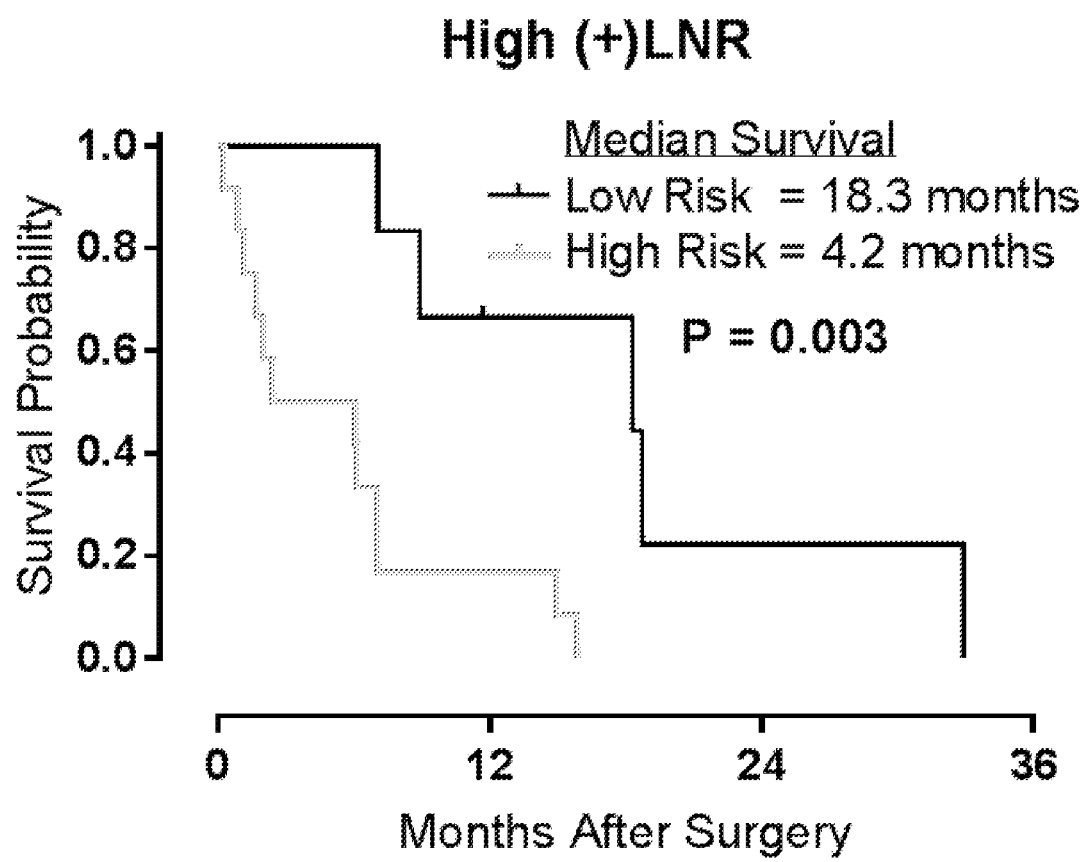

Next, experiments were conducted to determine if the protein signature has prognostic ability that is independent from possible confounding factors. The only factor that was significantly different between the groups was the positive lymph node ratio (pLNR). By splitting the pLNR at the median (0.14), two groups are created, low pLNR and high pLNR. FIG. 5A demonstrates that the patient population with a high pLNR the median survival in the high risk group is 4.2 months vs 18.3 months in the low risk group (p=0.003). FIG. 5B displays the low pLNR patients' survival curves for the high risk and low risk groups. The median survival of the high risk group is 10.7 months vs 42.7 months in the low risk group for patients with a low pLNR (p=0.003). Both the pLNR and Protein Risk Score remain significantly associated with survival on multivariate analysis. Thus the Protein Risk Score prediction model is not simply recapitulating what the pLNR is already telling us, but provides increased discrimination for survival at low and high positive lymph node ratios.

DISCUSSION

An 8-analyte signature of soluble protein concentrations taken from the tumor microenvironment is shown to predict overall survival in PDAC. Despite efforts to obtain better prognostic information for patients with pancreatic cancer, pre-operative risk factors are limited to clinical staging by imaging and CA19-9 levels. Superior prognostication depends upon risk factors only available post-operatively such as major vascular resection and number of tumor positive lymph nodes (Smith B J, et al. J Am Med Inform Assoc. 2014 21(e2):e203-11). Even then, these factors only contribute a small role in determining patient survival post-surgery.

To create this prognostic model, an analyte selection method was employed that accounted for a data set with over 15% of the variables significantly correlated with each other (P<0.01). This eliminated the inclusion of analytes that are associated with survival but do not provide increased discriminatory value from their covariates. These methods next prevented overfitting for data sets with large numbers of predictors or variables by penalization and shrinkage of the predictors, thus minimizing the risk of false discovery.

Several groups have tried to use markers such as circulating serum proteins (Torres C, et al. Pancreas. 2014 43(7):1042), serum neutrophil to lymphocyte ratios (Choi Y, et al. PLoS One. 2016 11(1):e0145692; Stotz M, et al. Br J Cancer. 2013 109(2):416-21), and other markers from pathology such as mircoRNAs (Lee K H, et al. Pancreas. 2015 44(5):764-8; Schultz N A, et al. World J Surg. 2012 36(11):2699-707; Li B S, et al. Genet Mol Res. 2015 14(4):16372-8; Khan M A, et al. Adv Exp Med Biol. 2015 889:71-87), protein levels (Chen L, et al. Sci Rep. 2014 4:5911), and RNA expression profiles (Bailey P, et al. Nature. 2016 531(7592):47-52) to predict prognosis in pancreatic cancer patients. However, there are inherent concerns with these studies using serum protein levels and neutrophil to lymphocyte ratios. These measurements may be influenced by other conditions such as chronic pancreatitis, concurrent infection, or prior surgeries such as a splenectomy or a roux-en-Y gastric bypass that may alter the serum protein profiles and circulating leukocyte numbers. Several groups have looked at markers from histologically processed tissues, but these histological analyses require subjective interpretation of positive and negative staining.

TABLE 1

Patient Clinicopathologic Information

| Parameter | N = 36 |
|---|---|
| Age, years | 71 (61-75) |
| Sex, male | 24 (67%) |
| Neoadjuvant Therapy | 10 (28%) |
| Total Lymph Nodes | 22 (19-30) |
| Positive Lymph Node Ratio (median, IQR) | 0.143 (0.044-0.244) (0.044-0.246) |
| CA 19-9, U/mL[1] | 148 (49-797) |
| Tumor Grade | |
| Well differentiated | 2 (6%) |
| Moderately differentiated | 17 (47%) |
| Poorly differentiated | 17 (44%) |
| Tumor Size, cm | 3.5 (2.6-4.4) |

TABLE 1-continued

Patient Clinicopathologic Information

| Margin Status | |
|---|---|
| R0 | 25 (69%) |
| R1 | 11 (31%) |
| Operation | |
| Pancreatoduodenectomy | 26 (72%) |
| Distal Pancreatectomy | 8 (22%) |
| Total Pancreatectomy | 2 (6%) |
| Stage | |
| T3 | 36 (100%) |
| N1 | 30 (83%) |
| Portal Vein Resection | 5 (14%) |
| Survival, months | 11.9 (6.8-23.7) |

Patient clinical parameters expressed as number (percentage) or median (IQR).
CA19-9 measured when the total bilirubin is less than 4 mg/dL.
R1 is defined as cancer cells within 1 mm of the surgical margin on pathological assessment.
[1]data missing from two patients;
IQR interquartile range

TABLE 2

Analyte association with overall survival

| Analyte | HR | 95% CI | p-value | Adjusted p-value |
|---|---|---|---|---|
| FGF-2 | 0.61 | 0.43-0.88 | 0.0072 | 0.2530 |
| IL-4 | 0.54 | 0.34-0.85 | 0.0082 | 0.2530 |
| G-CSF | 1.47 | 1.05-2.05 | 0.0247 | 0.2881 |
| Eotaxin | 0.63 | 0.42-0.95 | 0.0290 | 0.2881 |
| PDGF-AA | 1.45 | 1.00-2.09 | 0.0486 | 0.3404 |
| Flt-3L | 0.66 | 0.43-1.02 | 0.0607 | 0.3540 |
| TNF-alpha | 0.60 | 0.34-1.06 | 0.0798 | 0.3992 |
| RANTES | 0.56 | 0.28-1.11 | 0.0988 | 0.4321 |
| MDC | 0.71 | 0.47-1.08 | 0.1100 | 0.4321 |
| IL-13 | 0.71 | 0.46-1.10 | 0.1234 | 0.4321 |

Top 10 analyte associations with overall survival shown as a hazard ratio with single covariate p-values and adjusted p-values to correct for the expected false discovery rate with 35 covariates.
CI confidence interval;
HR hazard ratio

TABLE 3

Analyte coefficients

| Covariate | Penalized Coefficient | Unpenalized Coefficient |
|---|---|---|
| FGF-2 | −.287 | −.463 |
| Eotaxin | −.164 | −.466 |
| G-CSF | .280 | .491 |
| GM-CSF | .070 | .256 |
| IL-13 | −.125 | −.462 |
| IL-4 | −.725 | −.648 |
| IP-10 | −.036 | −.161 |
| RANTES | −.263 | −.360 |

Comparison of the eight non-zero penalized regression coefficients to conventional univariate coefficient estimates using standardized data.

TABLE 4

Univariate Analysis of Overall Survival

| Parameter | Reference | HR | 95% CI | p-value |
|---|---|---|---|---|
| Age (years) | 61-75 | 1.13 | 0.75-1.70 | 0.5712 |
| CA 19-9[1] | 49-797 | 1.32 | 0.92-1.90 | 0.1372 |
| Neoadjuvant Therapy | None | 1.04 | 0.46-2.39 | 0.9180 |
| Tumor Size | 2.6-4.4 | 1.10 | 0.80-1.52 | 0.5428 |
| Pathologic N Stage 1 | N Stage 0 | 1.58 | 0.54-4.56 | 0.3955 |

TABLE 4-continued

Univariate Analysis of Overall Survival

| Parameter | Reference | HR | 95% CI | p-value |
|---|---|---|---|---|
| # Positive Lymph Nodes | 1-6 | 1.99 | 1.22-3.24 | 0.0059 |
| Positive Lymph Node Ratio | 0.04-0.24 | 2.38 | 1.48-3.82 | 0.0004 |
| Grade | Moderate-Poor | 1.84 | 0.90-3.74 | 0.0937 |
| Procedure | | | | 0.0045 |
| | Distal Pancreatectomy-PD | 0.25 | 0.09-0.74 | |
| | Total Pancreatectomy-PD | 5.03 | 1.03-24.5 | |
| Positive Margin | Negative Margin | 2.40 | 1.10-5.21 | 0.0271 |
| PV Resection | No PV Resection | 2.90 | 1.03-8.12 | 0.0429 |

Continuous variable references are the 25th and 75th percentiles.
Displayed Hrs are for the values in the reference column.
If only one value in the reference column, the comparison is the parameter relative to the value in the reference column.
CA19-9 measured when the total bilirubin is less than 4 mg/dL.
Positive margin defined as cancer cells within 1 mm of the surgical margin on pathological assessment.
[1]data missing from two patients;
CI confidence interval;
HR hazard ratio;
PD pancreatoduodenectomy;
PV portal vein

TABLE 5

Patient Clinical Parameter In Low Risk vs High Risk Groups expressed as number (percentage) or median (IQR)

| Clinical Parameters | Low Risk N = 18 | High Risk N = 18 | P-value |
|---|---|---|---|
| Age, years | 69 (61-75) | 71 (61-75) | 0.556 |
| Neoadjuvant Therapy | 7 (39%) | 3 (17%) | 0.494 |
| Total Lymph Nodes | 26 (19-31) | 20.5 (17-26) | 0.124 |
| Positive Lymph Node Ratio | 0.09 (0.03-0.21) | 0.23 (0.06-0.31) | 0.026* |
| CA 19-9, U/mL | 115 (46-736) | 205 (85-749) | 0.465 |
| Tumor Grade | | | |
| Well Differentiated | 2 (11%) | 0 (0%) | 0.486 |
| Moderately Differentiated | 10 (56%) | 7 (39%) | 0.505 |
| Poorly Differentiated | 6 (44%) | 11 (61%) | 0.181 |
| Tumor Size, cm | 3.4 (2.7-4.0) | 3.6 (2.7-4.5) | 0.546 |
| Positive Margin | 4 (22%) | 7 (39%) | 0.471 |
| Operation | | | |
| Pancreatoduodenectomy | 12 (61%) | 14 (83%) | 0.711 |
| Distal Pancreatectomy | 6 (39%) | 2 (17%) | 0.229 |
| Total Pancreatectomy | 0 (0%) | 2 (11%) | 0.486 |
| Stage | | | |
| T3 | 18 (100%) | 18 (100%) | 1.000 |
| N1 | 14 (78%) | 16 (89%) | 0.658 |
| Portal Vein Resection | 1 (6%) | 4 (22%) | 0.148 |
| Survival, months | 24.1 (13.3-48.3) | 6.6 (2.1-10.9) | >0.001* |

P-values for continuous variables calculated using a students t-test and p-values for categorical variables were calculated using Fisher's exact test.
CA19-9 measured when the total bilirubin is less than 4 mg/dL. R1 is defined as cancer cells within 1 mm of the surgical margin on pathological assessment.
[1]data missing from two patients;
*indicated significant p-value
IQR interquartile range Example 2

The interaction between the malignant epithelial cells and surrounding tumor-associated stroma is the subject of intense investigation. The stromal component of PDAC represents as much as 80% of the overall tumor volume [Chu, G. C., et al., J Cell Biochem, 2007. 101(4):887-907]. The inflammatory milieu within the pancreatic cancer microenvironment correlates with clinicopathologic parameters, chemoresistance and survival [Delitto, D., et al., BMC Cancer, 2015. 15:783]. Experiments were therefore conducted to determine whether the pancreatic cancer microenvironment can distinguish PDAC from benign tissue.

Methods

Patient Sample Selection

Informed consent was obtained from all patients. Tissue samples were selected from a prospectively maintained tissue bank. Depending on the indication for operation, malignant or benign pancreatic tissue is collected from the surgical specimen at the time of surgical resection. All patients with pathologically confirmed PDAC were considered for this study. Patients who received neoadjuvant chemotherapy were excluded. Tumor tissue from patients with other malignant diagnoses of the pancreas were also excluded. Benign pancreatic specimens were collected from patients undergoing pancreatic resection or debridement for other indication. Due to the difficulty in collecting an equal number of benign specimens, thirty-one specimens were obtained from the Network for Pancreatic Organ Donors with Diabetes (nPOD). These specimens were resected at the time of organ donation in which the pancreas was unable to be used for donation. The clinicopathologic parameters of these patients were unavailable.

Tissue Collection and Preparation

All tissues were collected at the time of surgical resection. Samples were flash frozen and stored at −80° C. At the time of processing, tissues were thawed and weighed. Tissues were sharply divided into small pieces and placed into 2 mL lysing matrix D tubes (MP Biomedicals, Santa Ana, CA, USA). For every 30 mg of tissue, 500 µL of cell lysis buffer (Cell Signaling, Danvers, MA) was added. Samples underwent bead homogenization at 50 Hz for 40 seconds for three repetitions (Qiagen TissueLyser, Venlo, Netherlands). Samples were placed on ice for three minutes between each cycle. Lysates were collected and centrifuged at 13,000 RCF for 10 minutes. Supernatants were then collected and analyzed for total protein concentration (Pierce BCA Protein Assay Kit, Thermo Fisher Scientific, Waltham, MA, USA).

Soluble Protein Analysis

Homogenates were probed for 41 unique analytes using a 41-plex cytokine/chemokine assay per the manufacturer's protocol (Millipore Sigma, Burlington, MA, USA) and as previously described [Delitto, D., et al., BMC Cancer, 2015. 15:783]. Data was acquired with the MAGPIX system (Luminex Corporation, Austin, TX, USA) and analyzed using MILLI PLEX Analyst 5.1 (Millipore Sigma, Burlington, MA, USA). Individual protein concentrations were normalized to total protein concentration to yield individual analyte concentrations in pg/mg of tissue.

Results

Patient Clinicophathologic Information

Tumor tissue was collected from 82 patients with surgically resectable PDAC who did not receive neoadjuvant therapy. Patient clinicopathologic parameters are displayed in Table 6. Mean age was 69.7±9.1 years, 60% were male, and the majority were non-hispanic white. Oncologic factors, including stage, tumor differentiation, lymph node status, and margin status are additionally displayed in Table 6. The majority of patients had a pancreaticoduodenectomy.

TABLE 6

Patient Clinicopathologic Parameters

| Parameter | PDAC* (N = 82) | Benign (N = 77) |
|---|---|---|
| Age | 69.7 ± 9.10 | 54.2 ± 14.6 |
| Male | 50 (61.0%) | 21 (45.7%) |
| Race | | |
| White, non-hispanic | 74 (90.2%) | 38 (84.4%) |
| African American | 3 (3.7%) | 6 (13.3%) |
| Hispanic | 4 (4.9%) | 0 (0.0%) |
| Asian | 1 (1.2%) | 0 (0.0%) |
| American Indian | 0 (0.0%) | 1 (2.2%) |
| Pathology | | |
| PDAC* | 82 (100.0%) | 0 (0.0%) |
| Benign Pancreatic Tissue | 0 (0.0%) | 19 (24.7%) |
| Pancreatitis | 0 (0.0%) | 27 (35.1%) |
| Transplant Donor | 0 (0.0%) | 31 (40.2%) |
| Operation | | |
| Pancreatoduodenectomy | 69 (84.1%) | 0 (0.0%) |
| Distal Pancreatectomy | 11 (13.4%) | 15 (19.7%) |
| Total Pancreatectomy | 2 (2.44%) | 0 (0.0%) |
| Pancreatojejunostomy | 0 (0.0%) | 18 (23.7%) |
| Frey's Procedure | 0 (0.0%) | 12 (15.8%) |
| Puestow Procedure | 0 (0.0%) | 1 (1.3%) |
| Transplant donor | 0 (0.0%) | 31 (40.8%) |
| T Stage | | |
| T1 | 1 (1.2%) | |
| T2 | 4 (4.9%) | |
| T3 | 76 (92.7%) | |
| T4 | 1 (1.2%) | |
| N Stage | | |
| N0 | 15 (18.3%) | |
| N1 | 65 (79.3%) | |
| N2 | 2 (2.4%) | |
| Differentiation | | |
| Well | 6 (7.4%) | |
| Moderate | 40 (49.4%) | |
| Poor | 33 (40.7%) | |
| Undifferentiated | 2 (2.5) | |
| Positive Lymph Nodes | 3.9 ± 3.89 | |
| Total Lymph Nodes | 22.4 ± 7.51 | |
| Lymph Node Ratio | 0.17 ± 0.165 | |
| Tumor Size (cm) | 3.69 ± 1.862 | |
| Lymphovascular Invasion | 68 (82.9%) | |
| Perineural Invasion | 81 (98.8%) | |
| R0 Resection | 62 (76.0%) | |

*PDAC: Pancreatic ductal adenocarcinoma

Benign pancreatic tissue was collected from 77 patients undergoing pancreatic resection for other pathology. Patient clinicopathologic parameters are displayed in Table 7. The average age was 54.2±9.1 years, 45.7% were male, and the majority were non-hispanic white. Thirty one specimens (40.8%) were obtained from unused pancreata from deceased transplant donors. Twenty seven patients underwent surgery for pancreatitis. The remaining benign specimens were collected at the time of pancreatic resection for other indication.

TABLE 7

Change to recursive partitioning

| | | Prediction by AUC 'Metagene' | |
|---|---|---|---|
| | | Other | PDAC |
| Tissue Source | Other | 69 | 8 |
| | PDAC | 9 | 77 |

Heatmap and Area Under the Curve Analysis

Figure 8A:
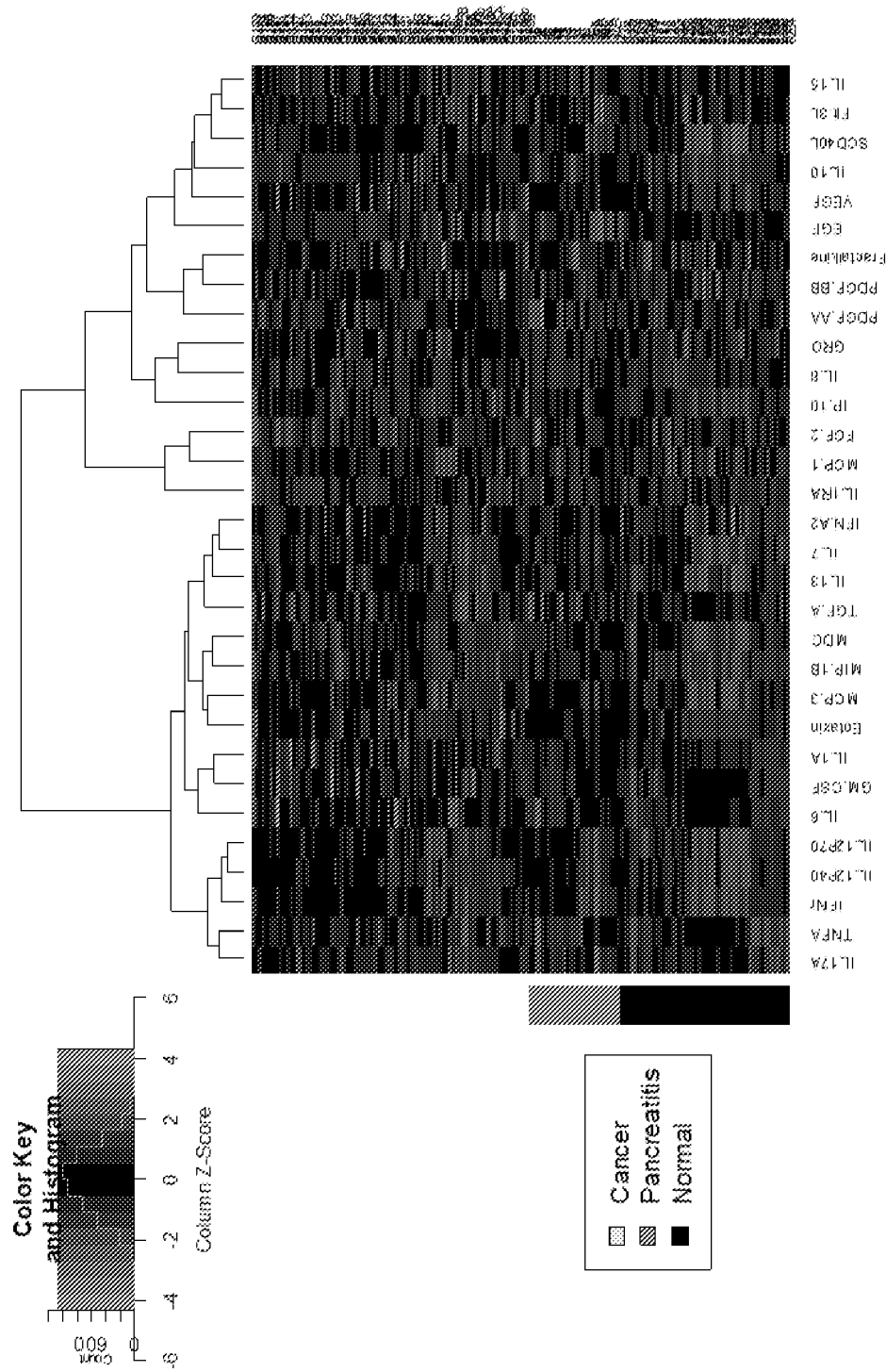
FIGS. 8A and 8B are single-cluster (FIG. 8A) and double-cluster (FIG. 8B) heat maps showing shows that pancreatitis looks like cancer for IL-17A through IFN-A2 and more like benign tissue for the right cluster IL-1RA through IL-15.
Figure 8B:
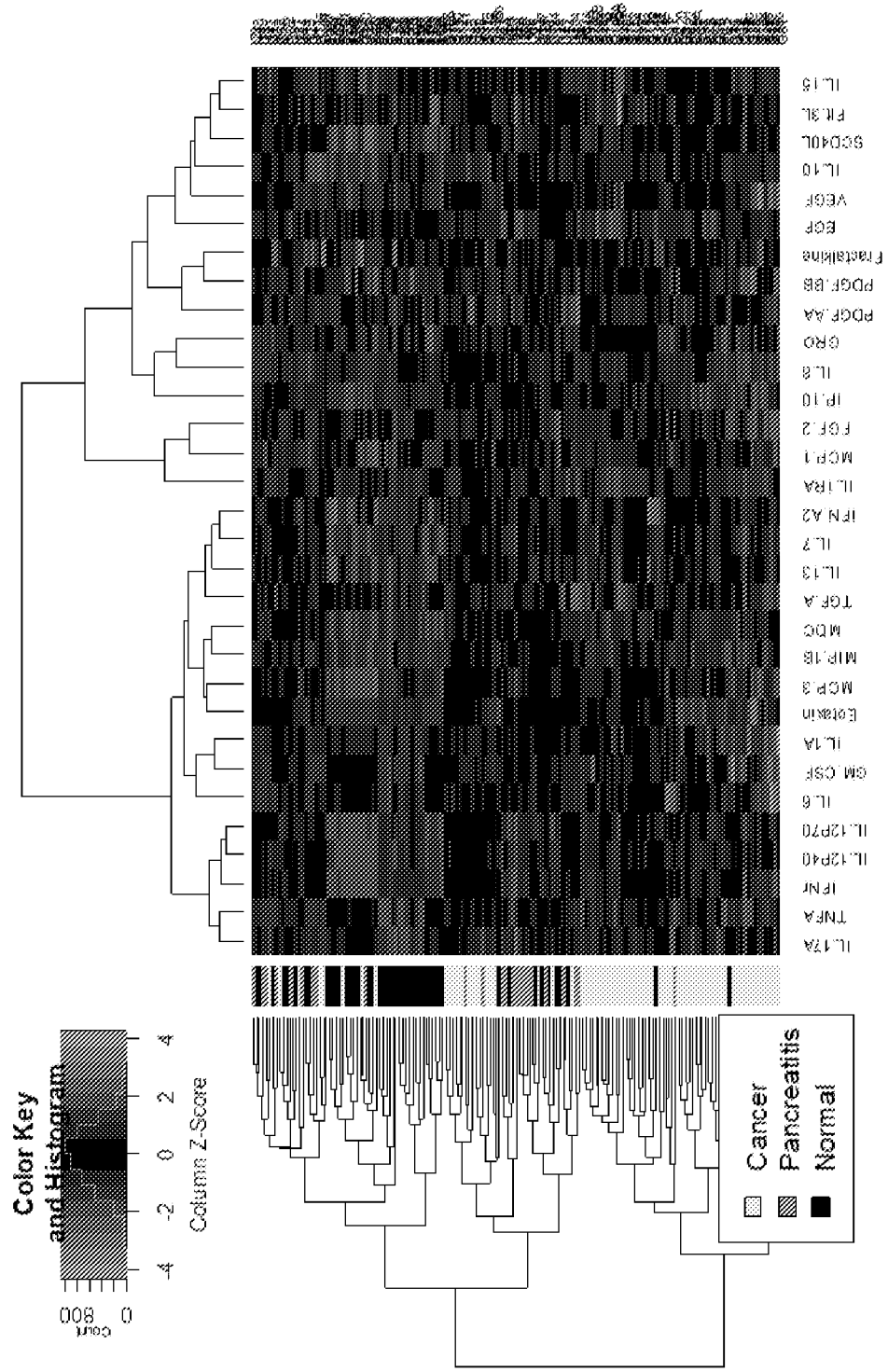
Figure 9:
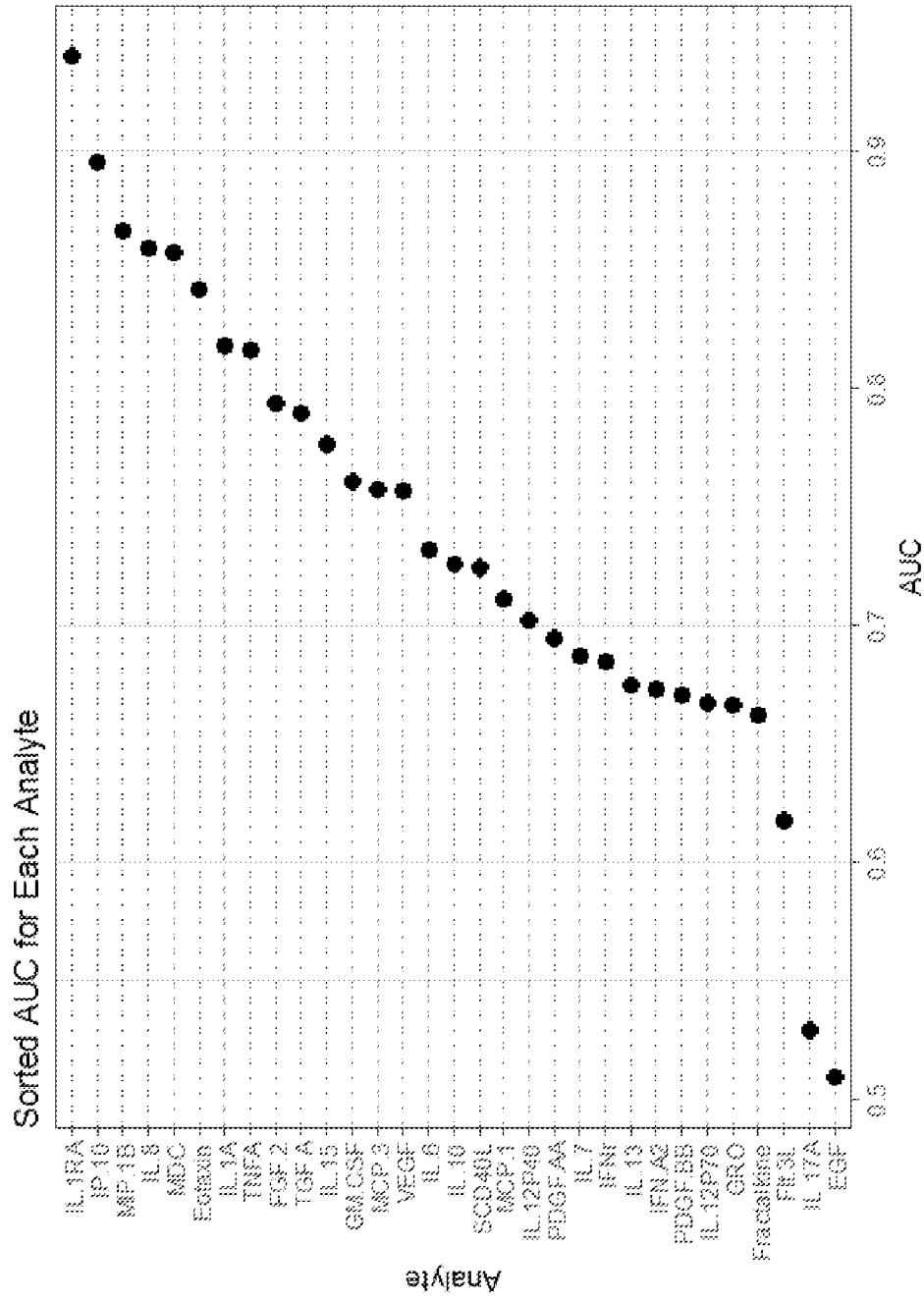
FIG. 9 shows variable importance for distinguishing cancer from non-cancer [normalized to total protein].

Of the 41 analytes assayed, 31 were used for analysis. Analytes were excluded if the concentration was less than the lower limits of the standard curve in greater than 20% of samples. Analyte concentrations were logged and standardized with a mean of zero and stage PDAC, pancreatitis, and benign samples tend to cluster together, although there are outliers. FIG. 9 demonstrates sorted area under the curve (AUC) for each of the thirty-one analytes. Fourteen had an AUC of greater than 0.75 for distinguishing PDAC from benign tissue (FIGS. 8A and 8B). Interleukin-1 Receptor Antagonist (IL-1RA) had an AUC>0.95.

Recursive Partitioning

Recursive partitioning was performed on logged and standardized data to differentiate PDAC from benign tissue. The model was run three times to separately optimize for accuracy, sensitivity, and specificity. Table 7 summarizes the predicted vs. observed cases of PDAC and benign tissue using the three models.

Figure 10A:
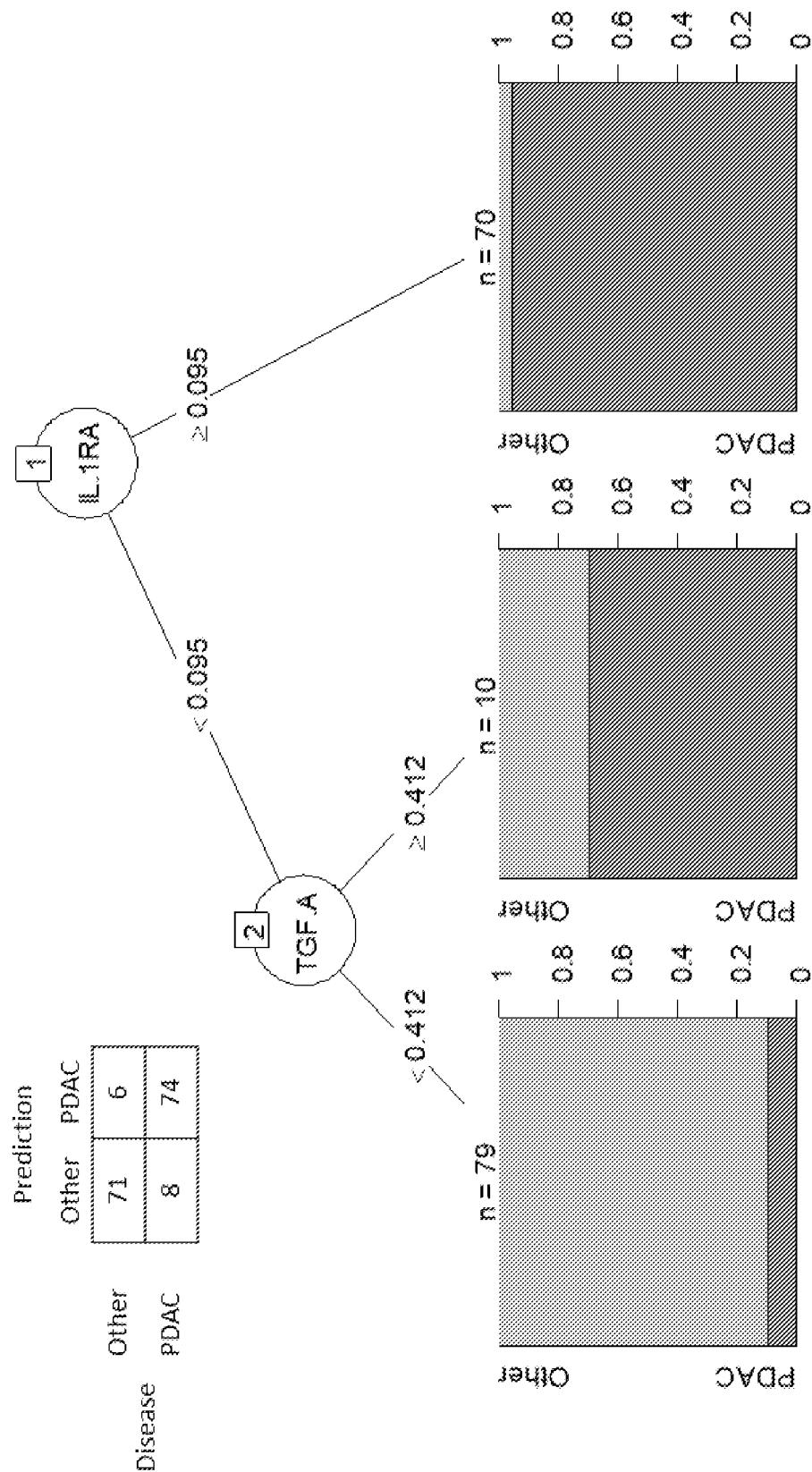
FIG. 10A shows a two class problem: PDAC vs other. Default treats each misclassification equally, essentially optimizing for accuracy.
Figure 10B:
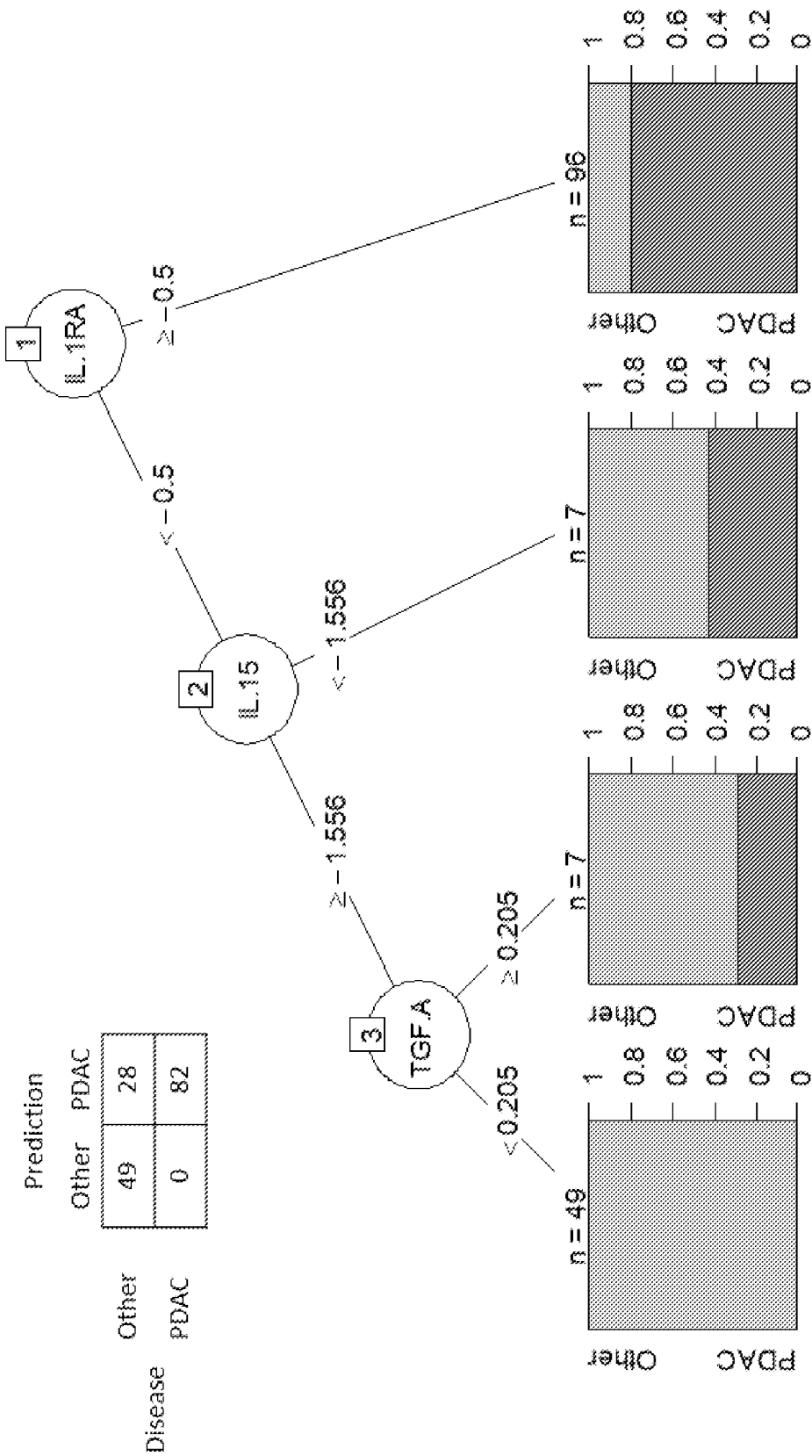
FIG. 10B shows optimization for specificity. Missing a case of PDAC (false negative classification) is considered costlier than incorrectly diagnosing benign disease as cancer (false positive classification). In this partitioning model the weight of a false negative is five times the weight of a false positive. By adding IL-15 to the mix, the false negative rate is reduced from 11% to 0%.
Figure 10C:
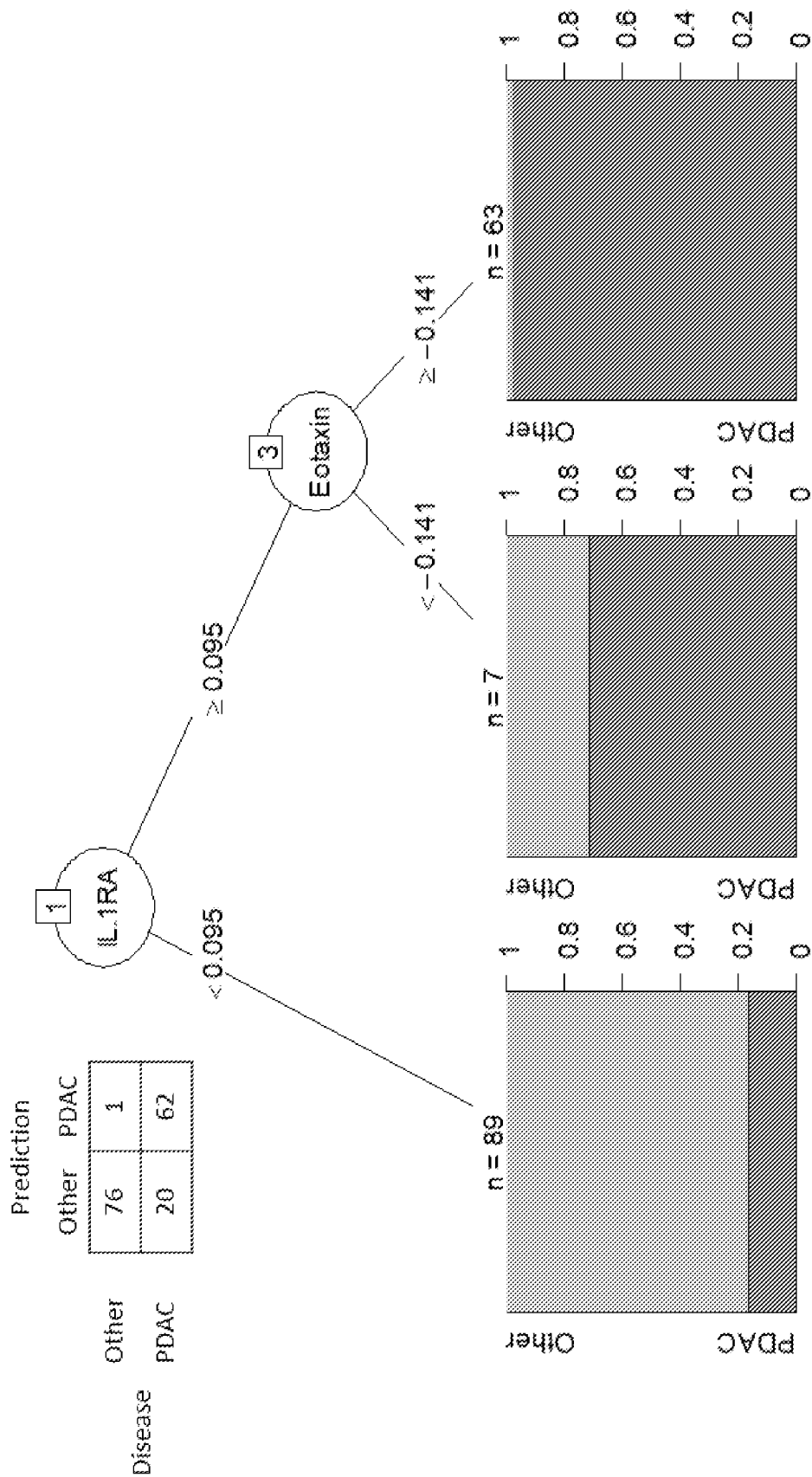
FIG. 10C shows the opposite weighting: a FP is 5× as important as a FN (optimizing for sensitivity and NPV). The chart shows 20 FN, 1 FP.
Figure 11:
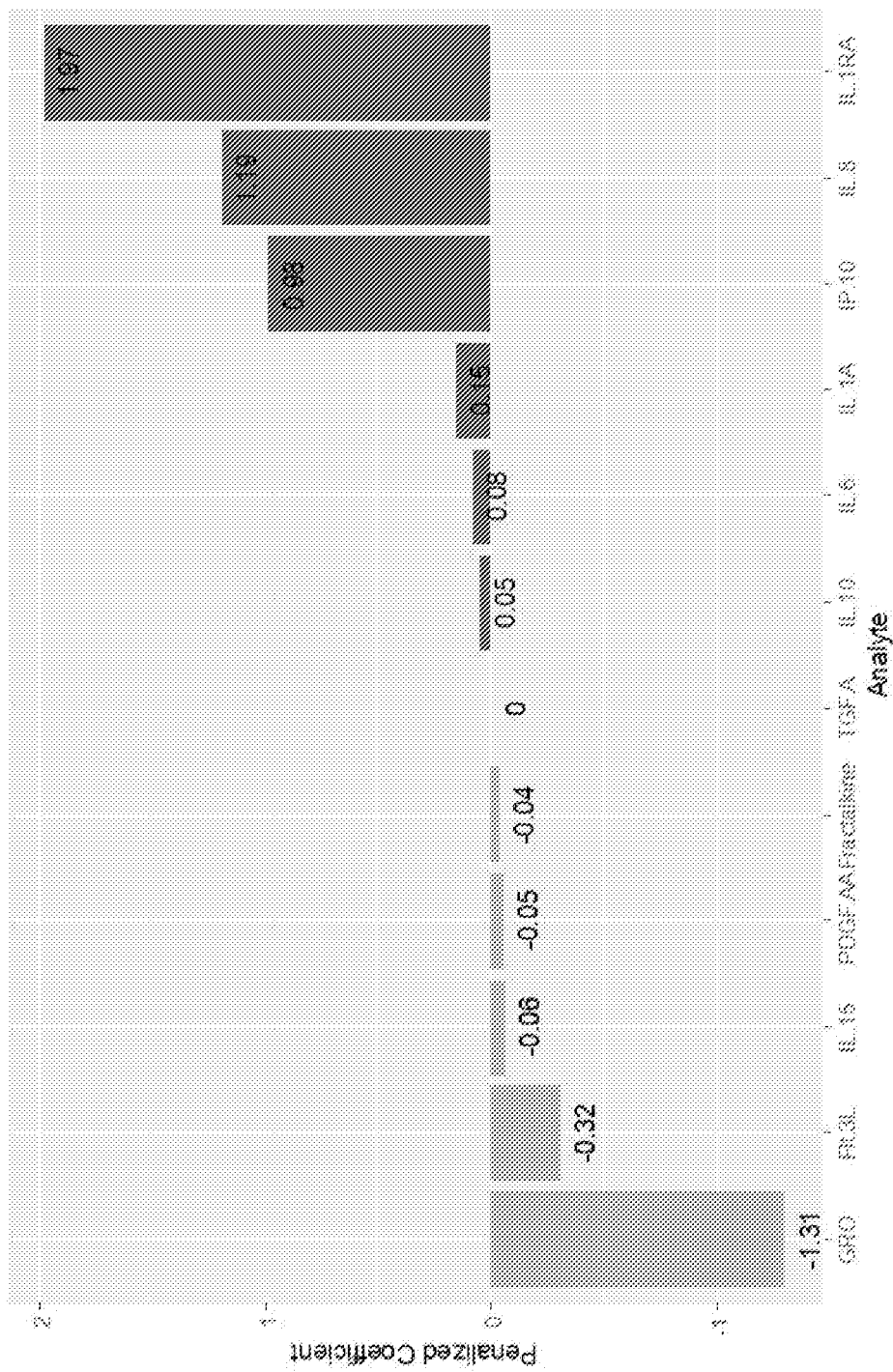
FIG. 11 shows revised listing of coefficients. The intercept is excluded. Twelve non-zero coefficients are displayed although the coefficient for TGF-α is miniscule (0.002). Interestingly, TGF-α is important in recursive partitioning. The difference is due to conditioning. In the classification tree, TGF-α is conditional on IL-1RA and/or IL-15. In the penalized regression, TGF-α is conditional jointly on all other analytes in the model.
Figure 12A:
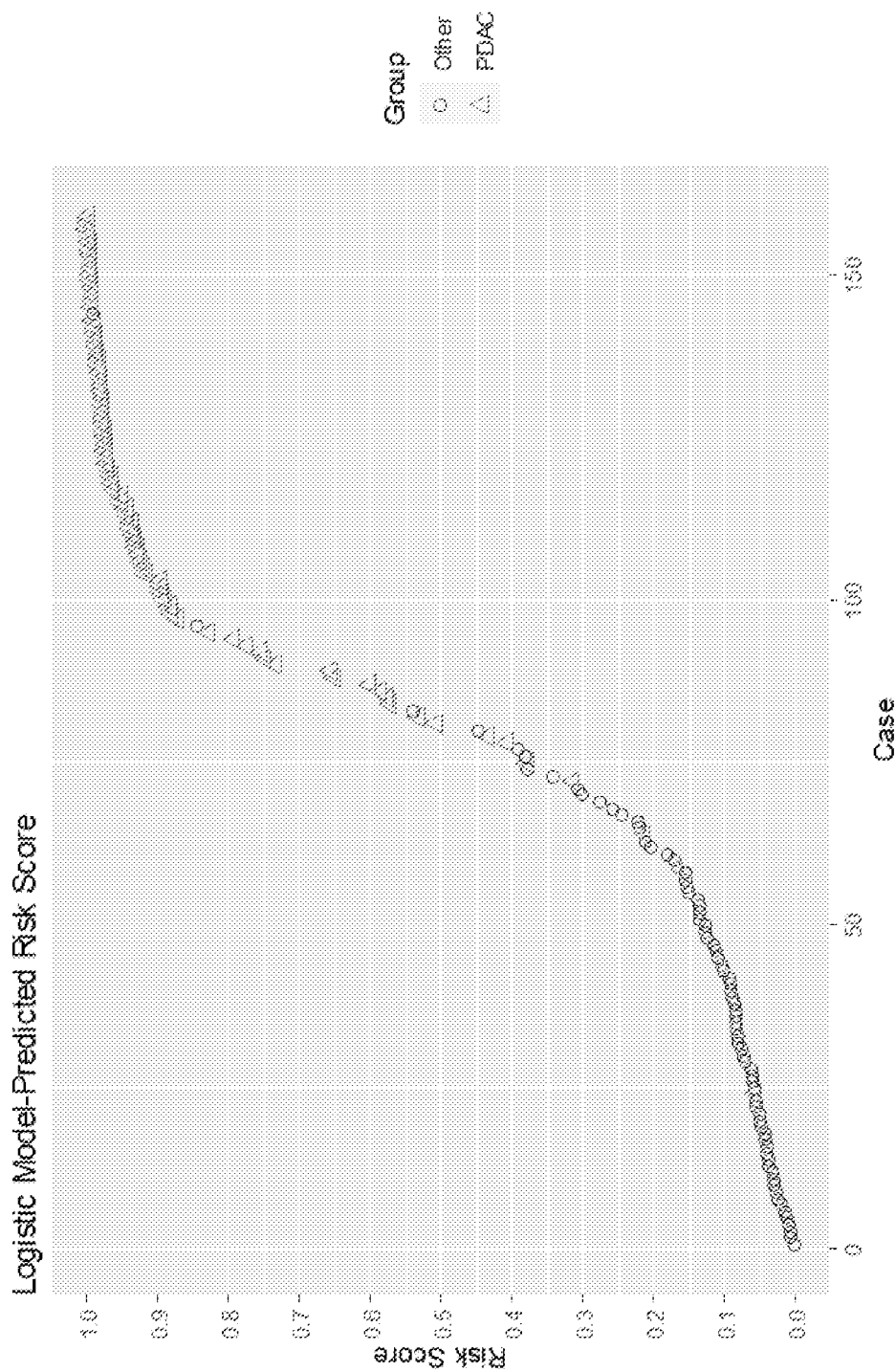
FIG. 12A shows a Risk Score defined as the predicted probability that a case is PDAC based on the penalized logistic regression model. Symbols denote the actual tissue type (PDAC or other).
Figure 12B:
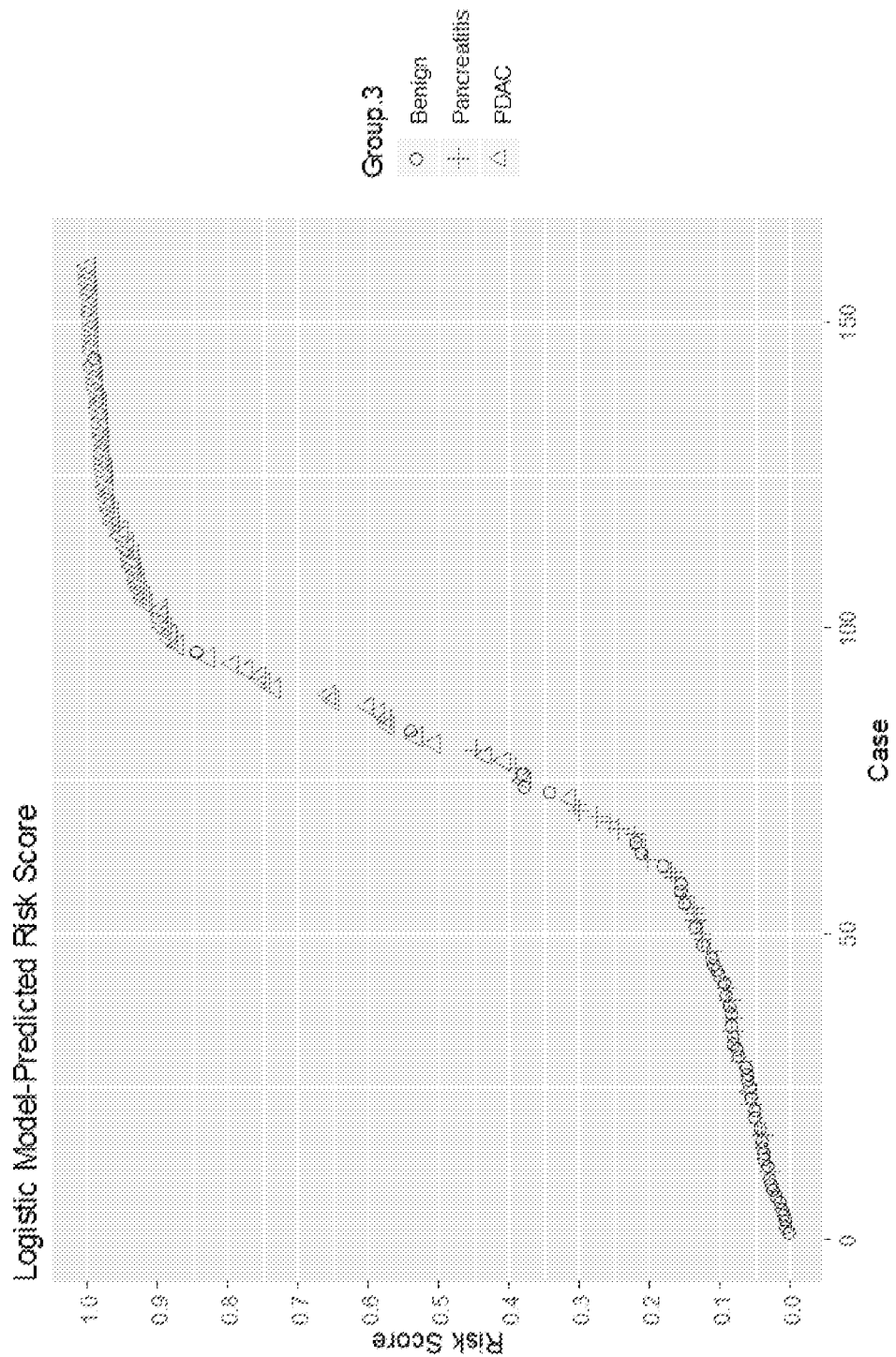
FIG. 12B shows that using the original 3 categories of tissue type, pancreatitis is among the benign specimens.
Figure 13B:
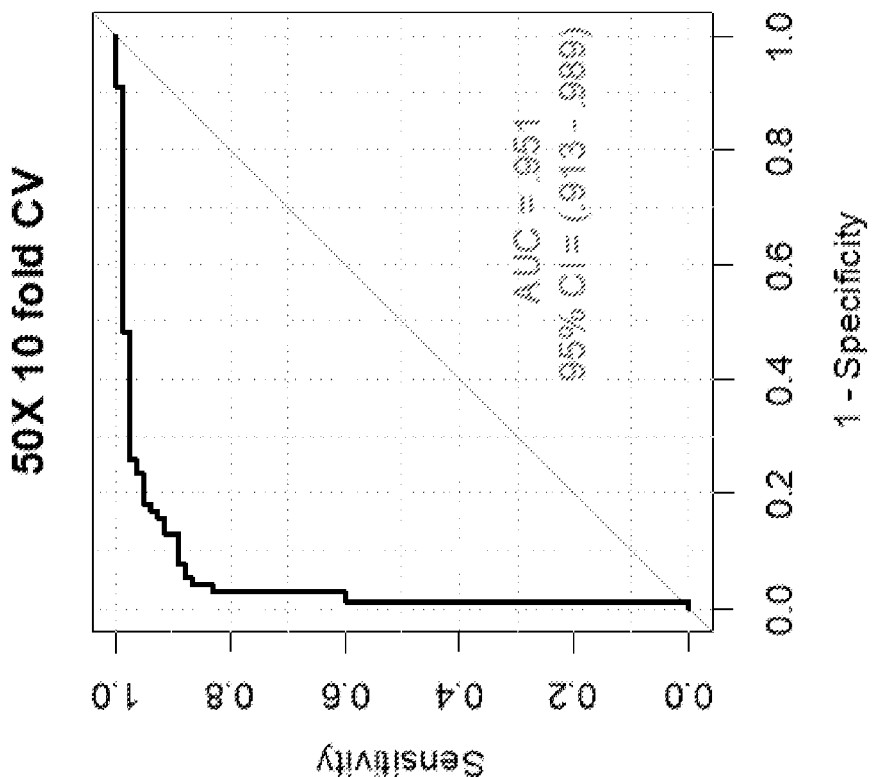
FIG. 13B is a ROC curve for the average of 50 10-fold cross validations. There was only a slight decrease in AUC of 0.975-0.951=0.024.
Figure 13A:
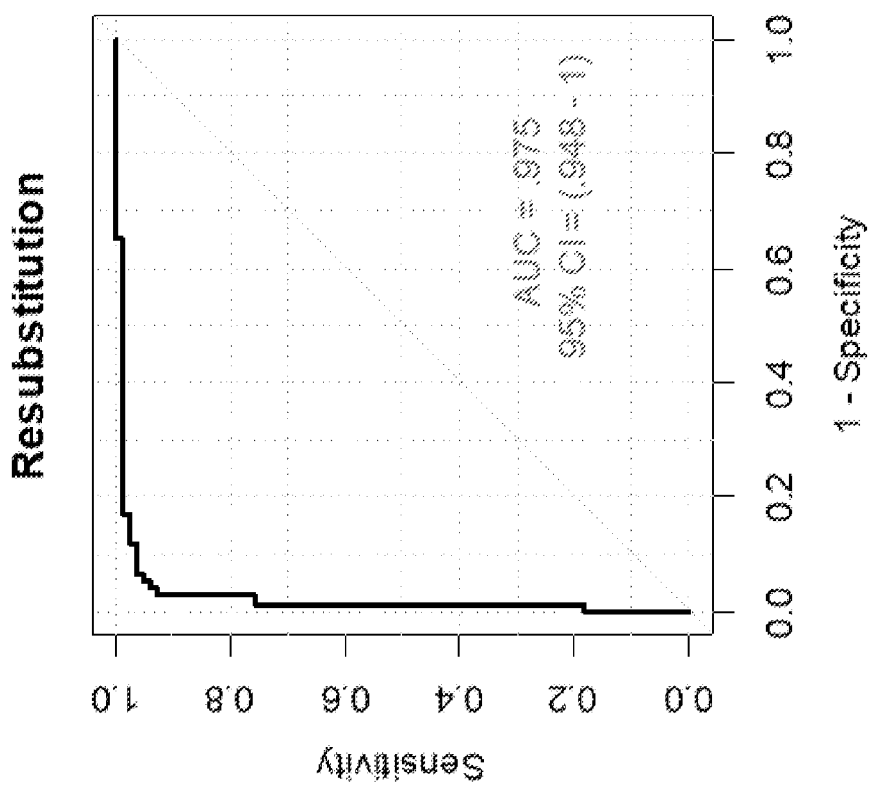
FIG. 13A is a ROC for the original penalized model using 14 analytes.

FIGS. 10A to 10C demonstrates the recursive partitioning model optimized for accuracy. An IL-1RA level≥0.095 correctly classified 68 of 70 cases as PDAC. An IL-1RA≤0.095 and transforming growth factor alpha (TGF-α)<0.412 correctly identified 71/79 cases as benign. Of the remaining 10 cases with IL-1RA≤0.076 and TGF-α≥0.412, 7/10 were PDAC. The accuracy of this classification method was 91.2%. Sensitivity and specificity were 90.2% and 92.2%, respectively. Positive predictive value (PPV) and negative predictive value (NPV) were 92.5% and 89.9%, respectively. FIG. 10C demonstrates the recursive partitioning model optimized for sensitivity. In this model, the weight of a false negative is five times the weight of a false positive. A third node, interleukin-15 (IL-15) is incorporated in this model. The sensitivity of this model improved to 100%. There were no false negatives. The accuracy, specificity, PPV, NPV were 82.4%, 74.6%, 63.6%, and 100%, respectively. FIG. 10B demonstrates the recursive partitioning model optimized for specificity. In this model, the weight of a false positive is five times the weight of a false negative. The nodes included IL-1RA and eotaxin. The specifity of this model improved to 98.4%. There was a single false positive. The accuracy, sensitivity, PPV, and NPV was 86.8%, 79.2%, 98.7%, and 75.6%, respectively. OK Penalized Logistic Regression Model A penalized logistic regression model was used to asses for analytes that may hold diagnostic utility on multivariate analysis (FIG. 11). Twelve of the thirty one analytes had non-zero coefficients. This method demonstrated a receiver operating curve (ROC) with an AUC of 0.975 (95% CI: 0.948-1) (FIG. 13A). The ROC curve for the average of 50 10-fold cross validations is displayed in FIG. 13B. The AUC decreased slightly to 0.951 (95% CI: 0.913-0.989).

Figure 14A:
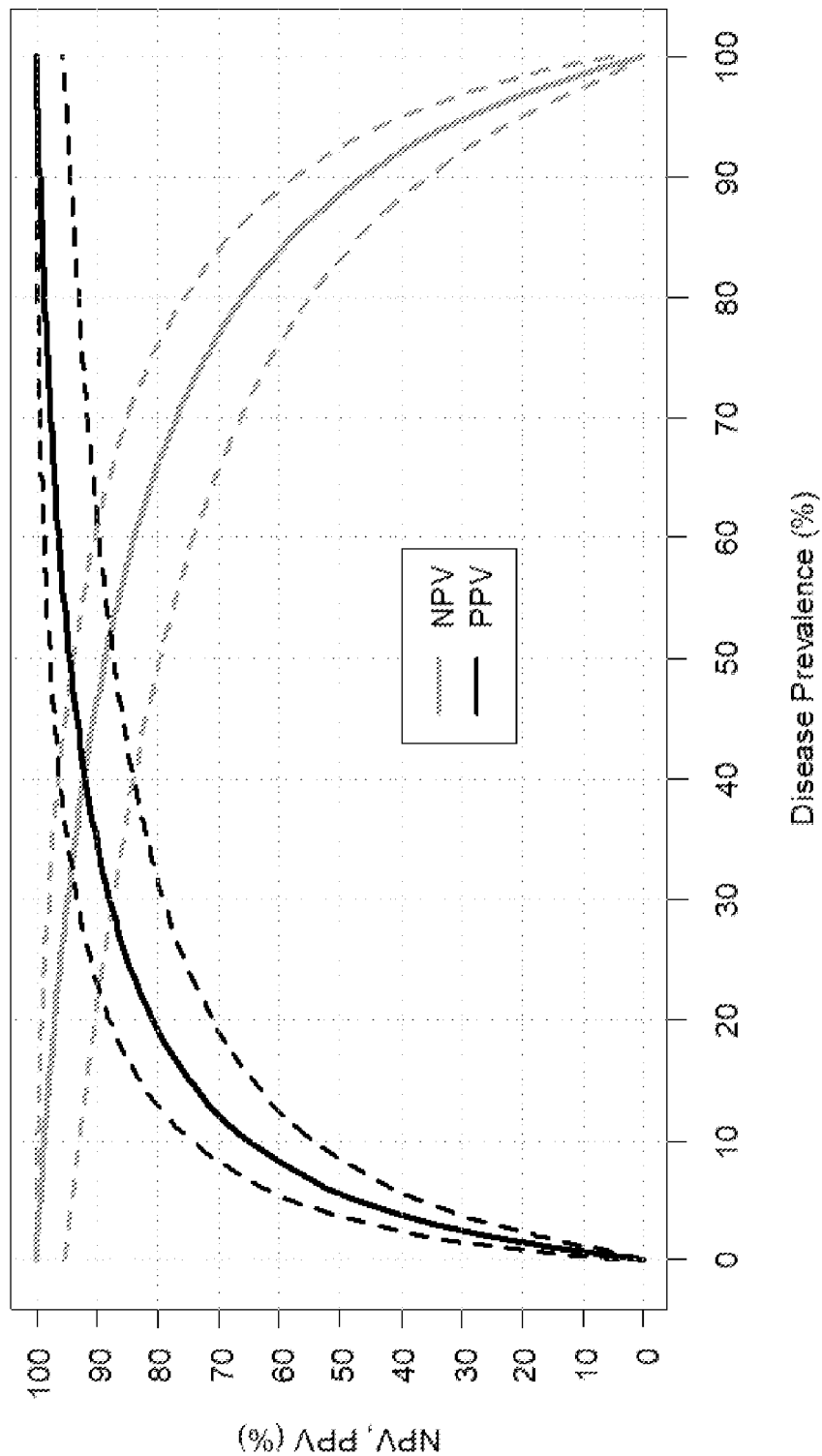
FIG. 14A. For any disease prevalence (as an example, in a clinical practice this could be the proportion of confirmed PDAC among all cases with indeterminate cytology), the black curve shows estimated PPV; the dashed lines are 95% confidence bands.
Figure 14B:
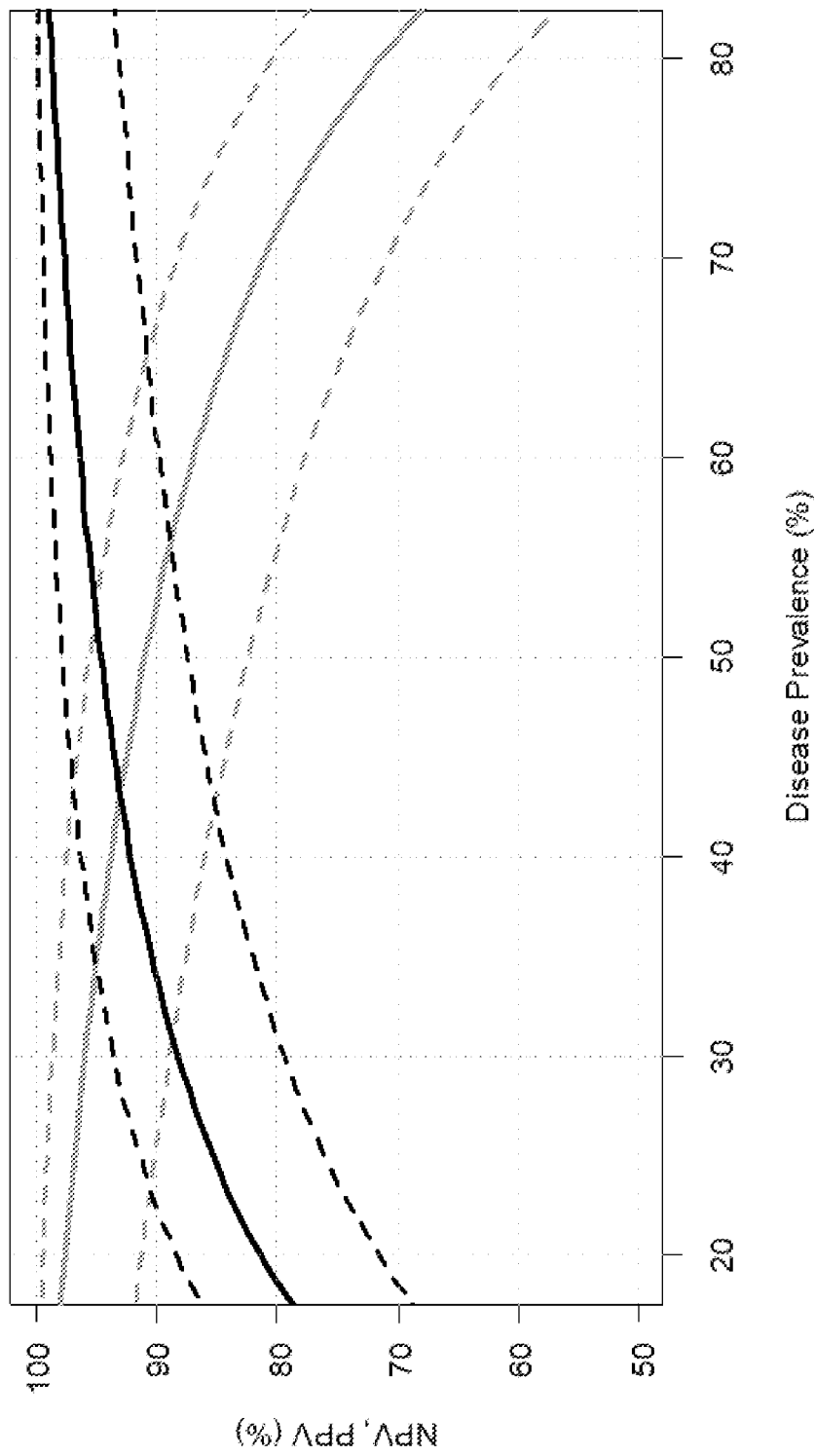
FIG. 14B is an enlarged view of a portion of FIG. 14A with added grid lines at 5% intervals.
Figure 15:
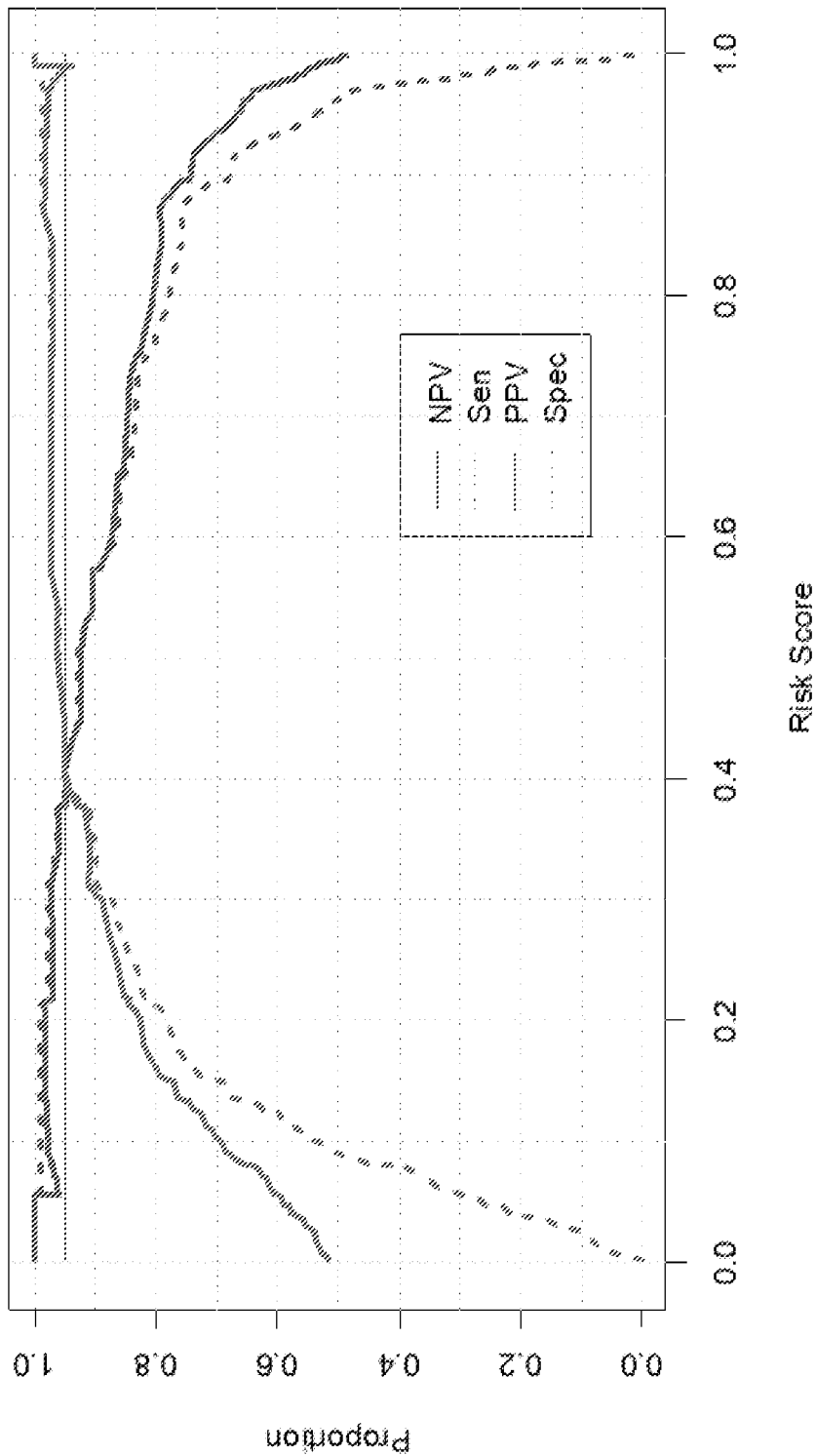
FIG. 15 is an alternate way to view the tradeoffs in varying the risk score cutoff. Increasing the cutoff increases both specificity and PPV and decreases the sensitivity and NPV. The crossover at 0.4 is the most accurate cutoff. The horizontal red line indicates a 95% target for any characteristic. Sliding the cutoff downward to effectively label more cases as positive (and increase sensitivity) only achieved as marginal improvement in sensitivity (~2-3%), while quickly leading to rapid decline in specificity. This is because the most accurate cutoff has roughly equal sensitivity (0.951) and specificity (0.948).
Figure 16:
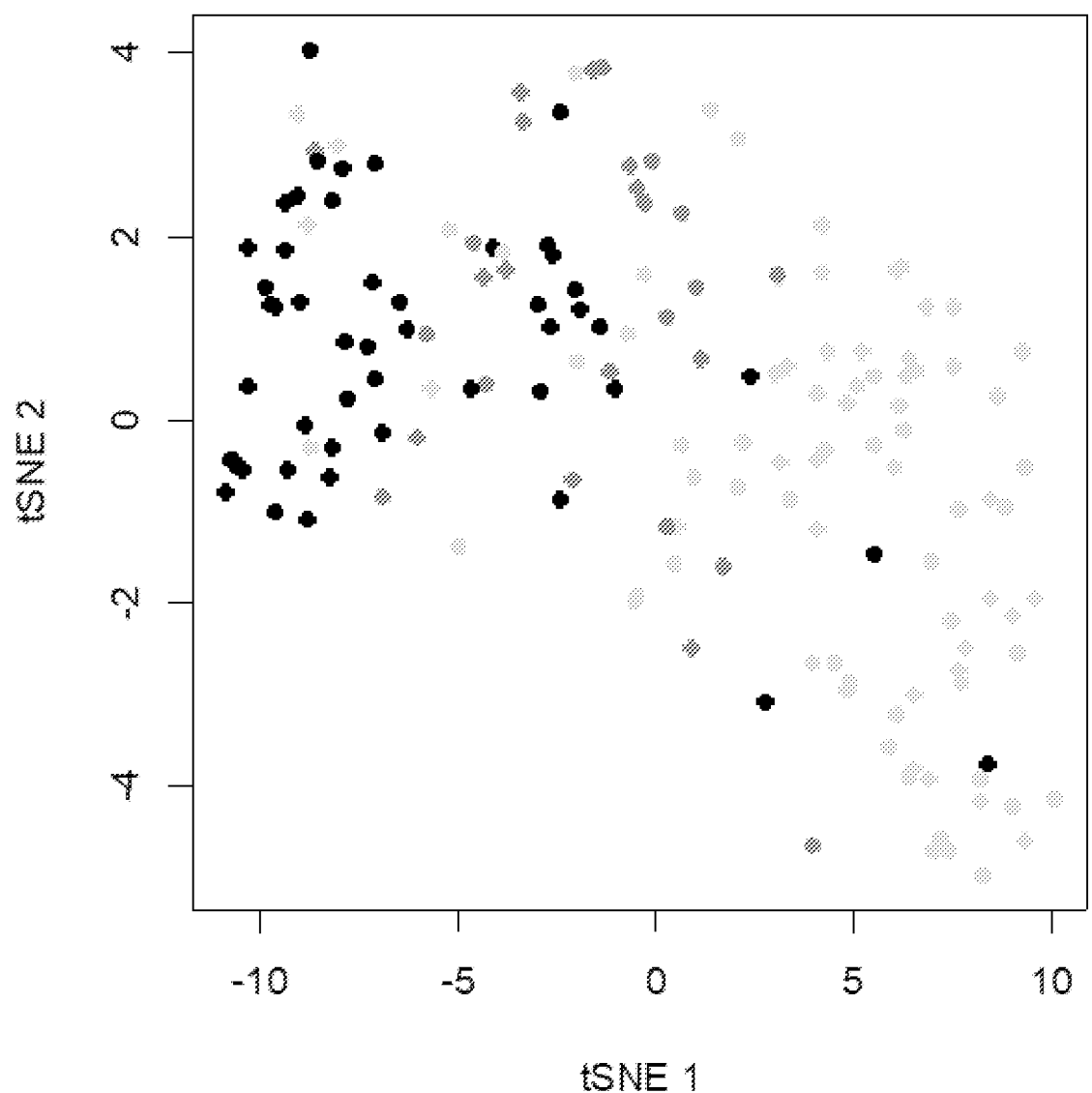
FIG. 16 shows is a tSNE plot using the scheme light gray for PDAC, dark gray for pancreatitis, and black for normal (t distributed stochastic neighbor embedding). There is some separation, albeit imperfect between normal (top left) and PDAC (bottom right) with pancreatitis in the middle. There are 31 non-missing analytes so this plot projects the cases in 31-dimensional space onto two dimensions in such a way that distances in high dimensional space are preserved in the projection.
Figure 17:
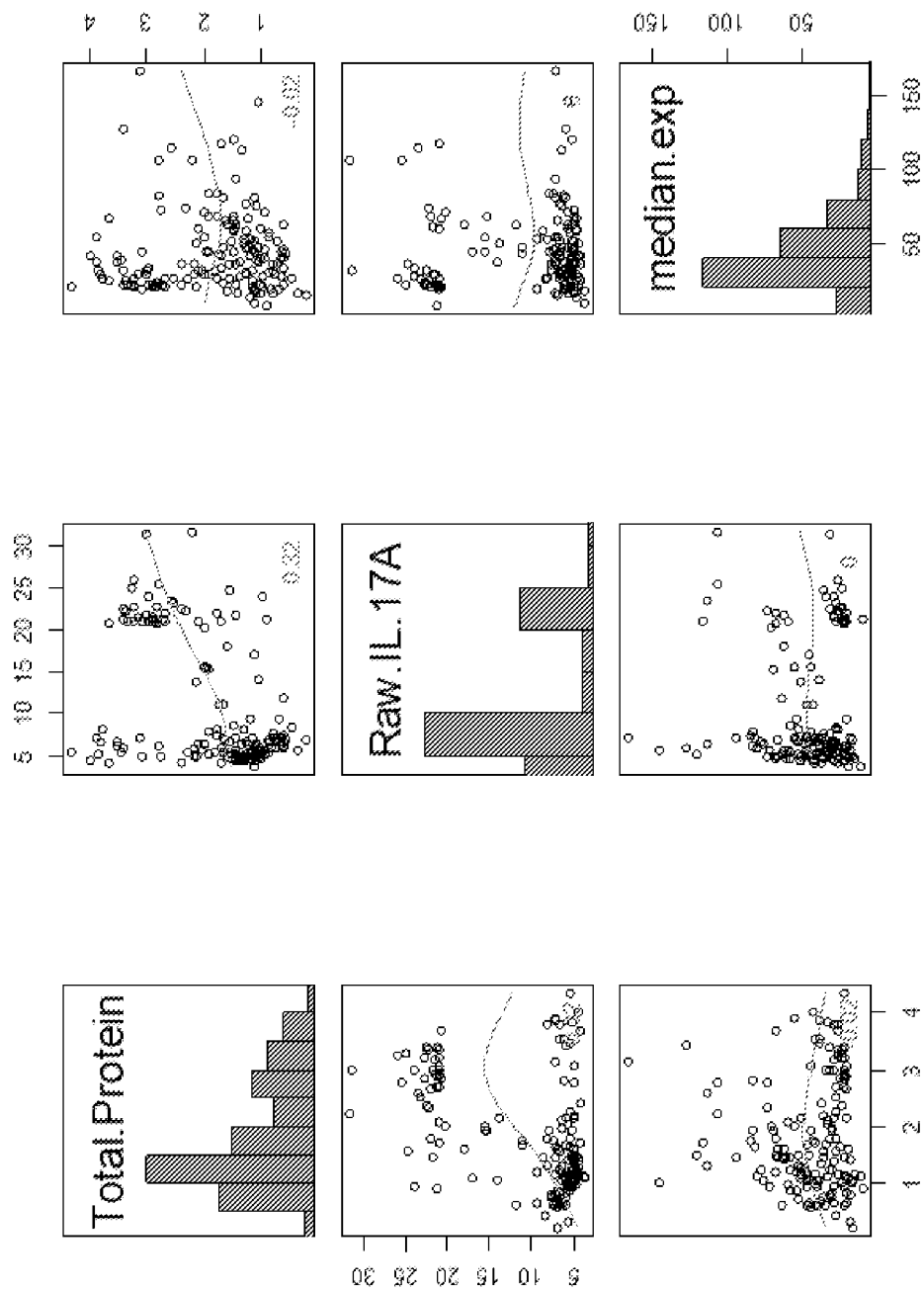
FIG. 17 is a scatterplot matrix showing distributions (diagonal) and correlations (off diagonal) of three normalizing candidates. Number in bottom right is the Spearman correlation coefficient; red if p s 0.01, blue otherwise.
Figure 18A:
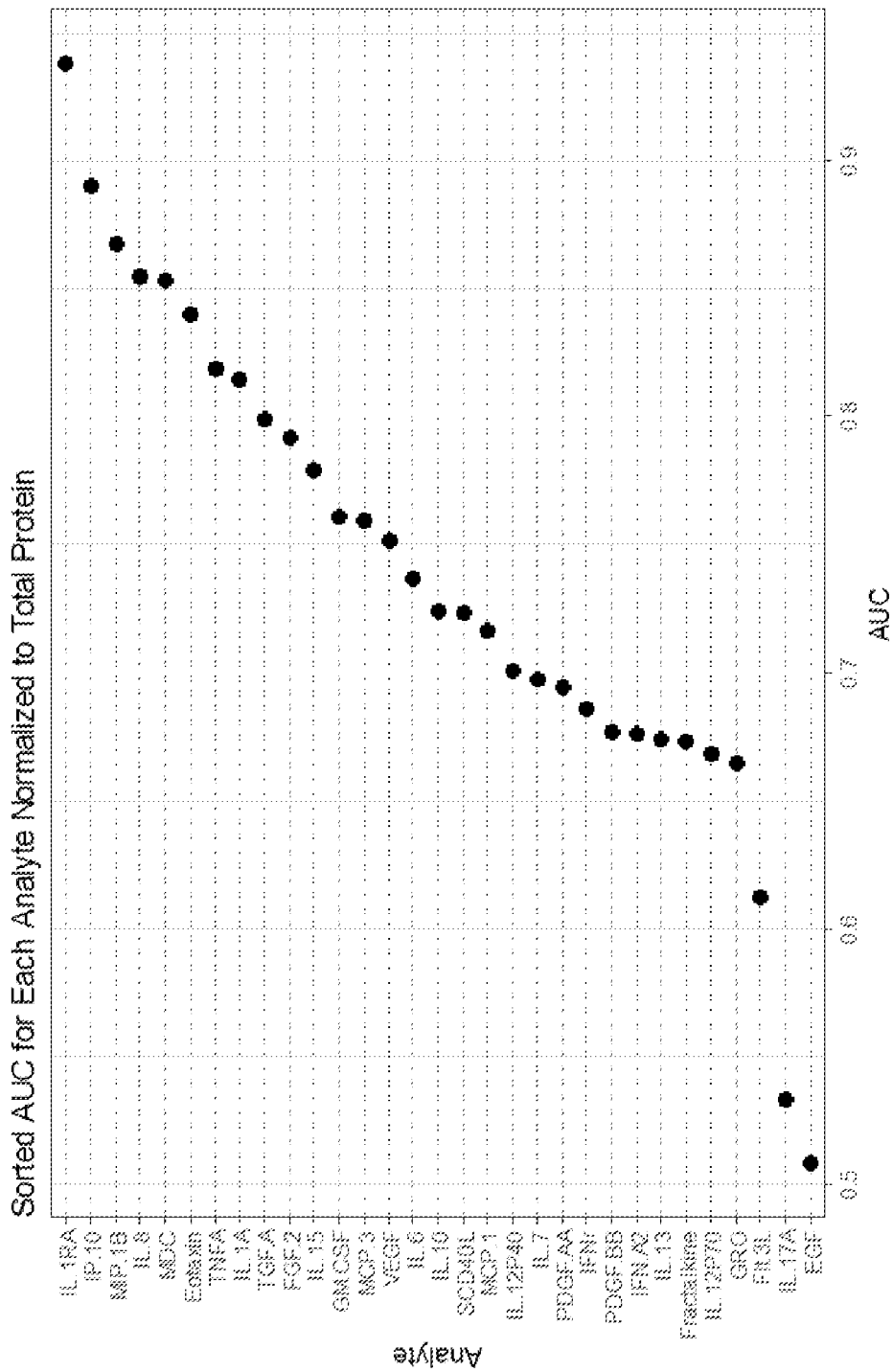
FIGS. 18A to 18D are sorted AUC for each analyte normalized to total protein (FIG. 18A), using raw data (FIG. 18B), normalized to IL-17A (FIG. 18C), and normalized to median expression (FIG. 18D).
Figure 18B:
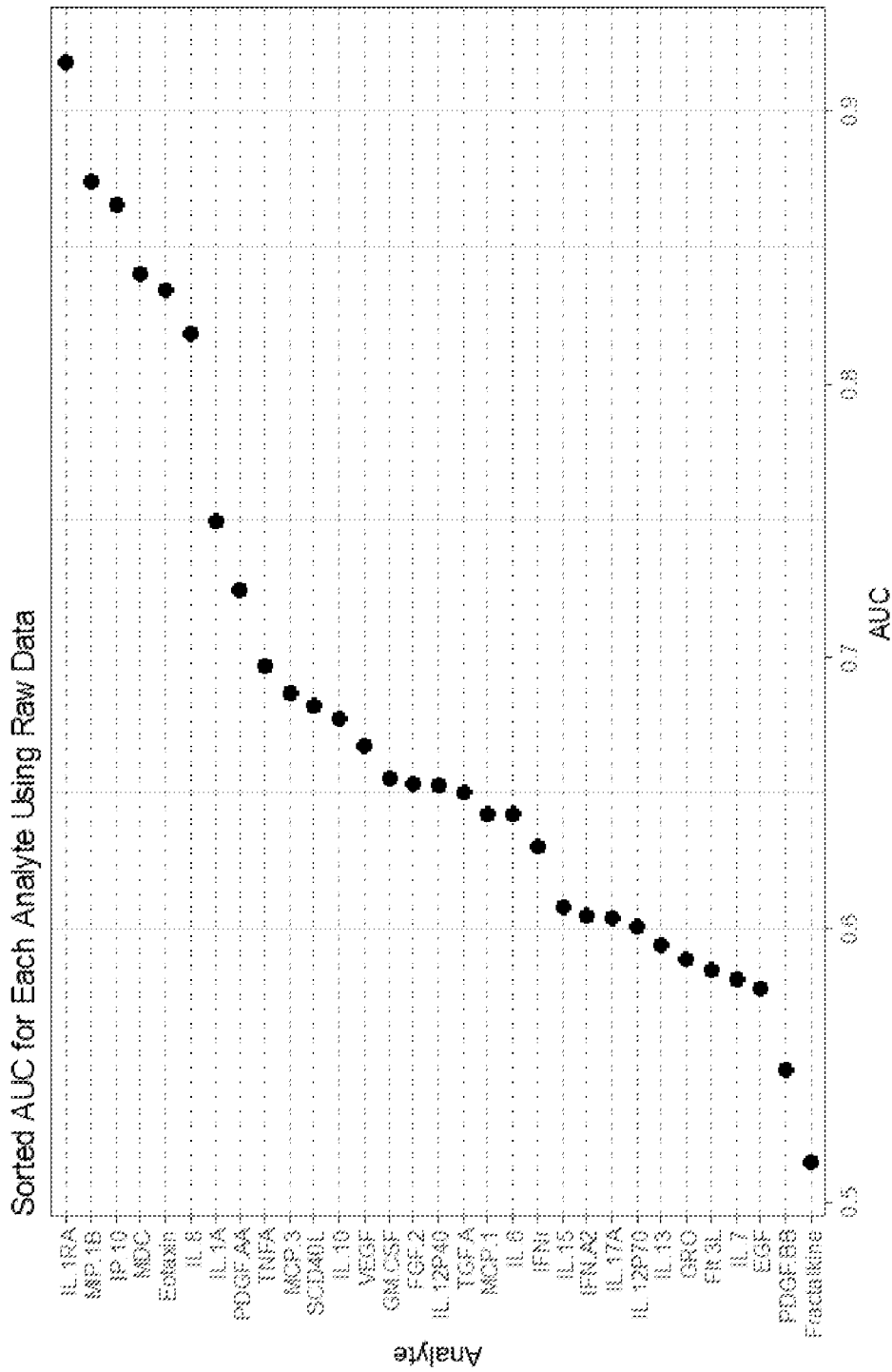
Figure 18C:
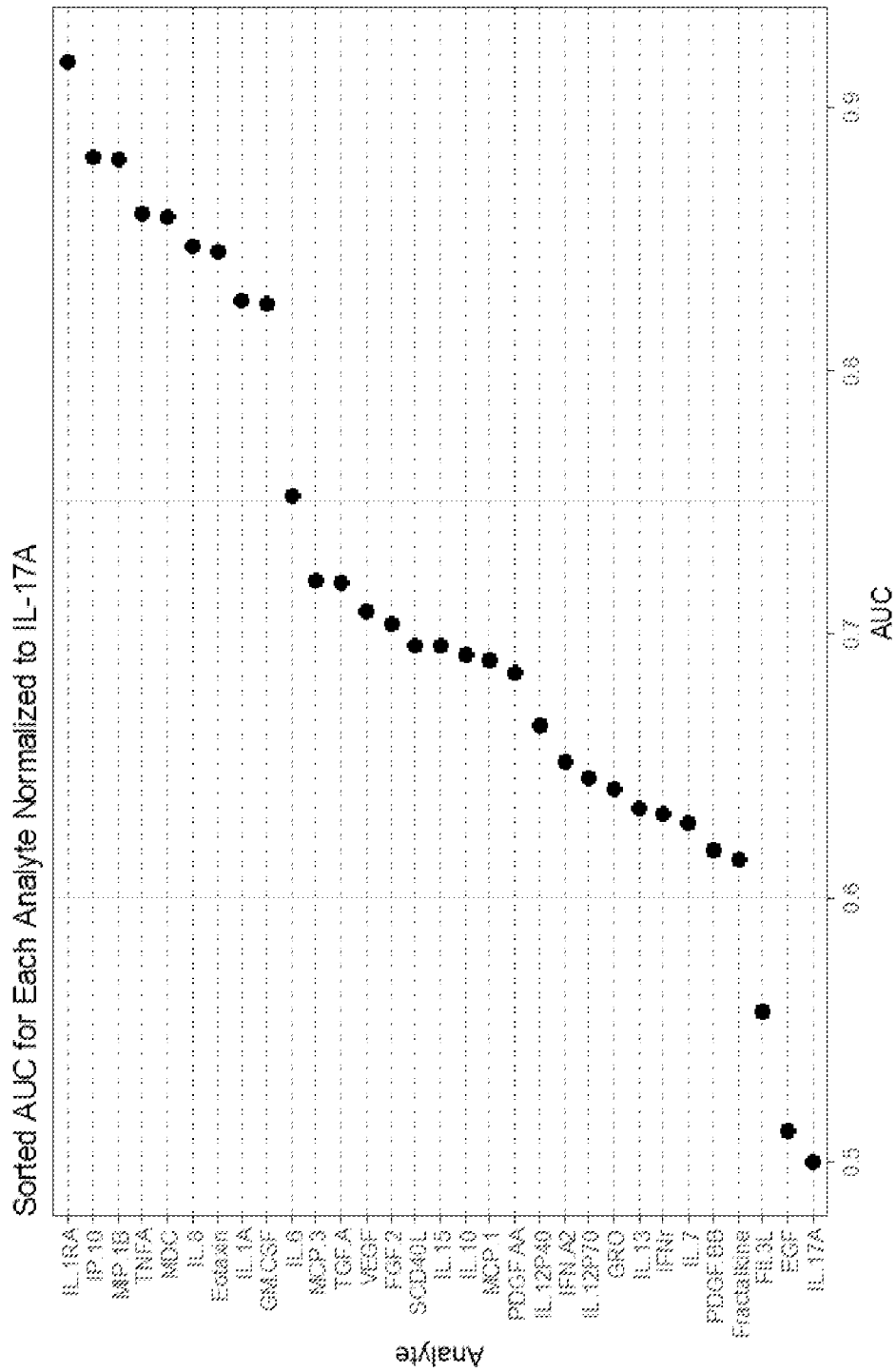
Figure 18D:
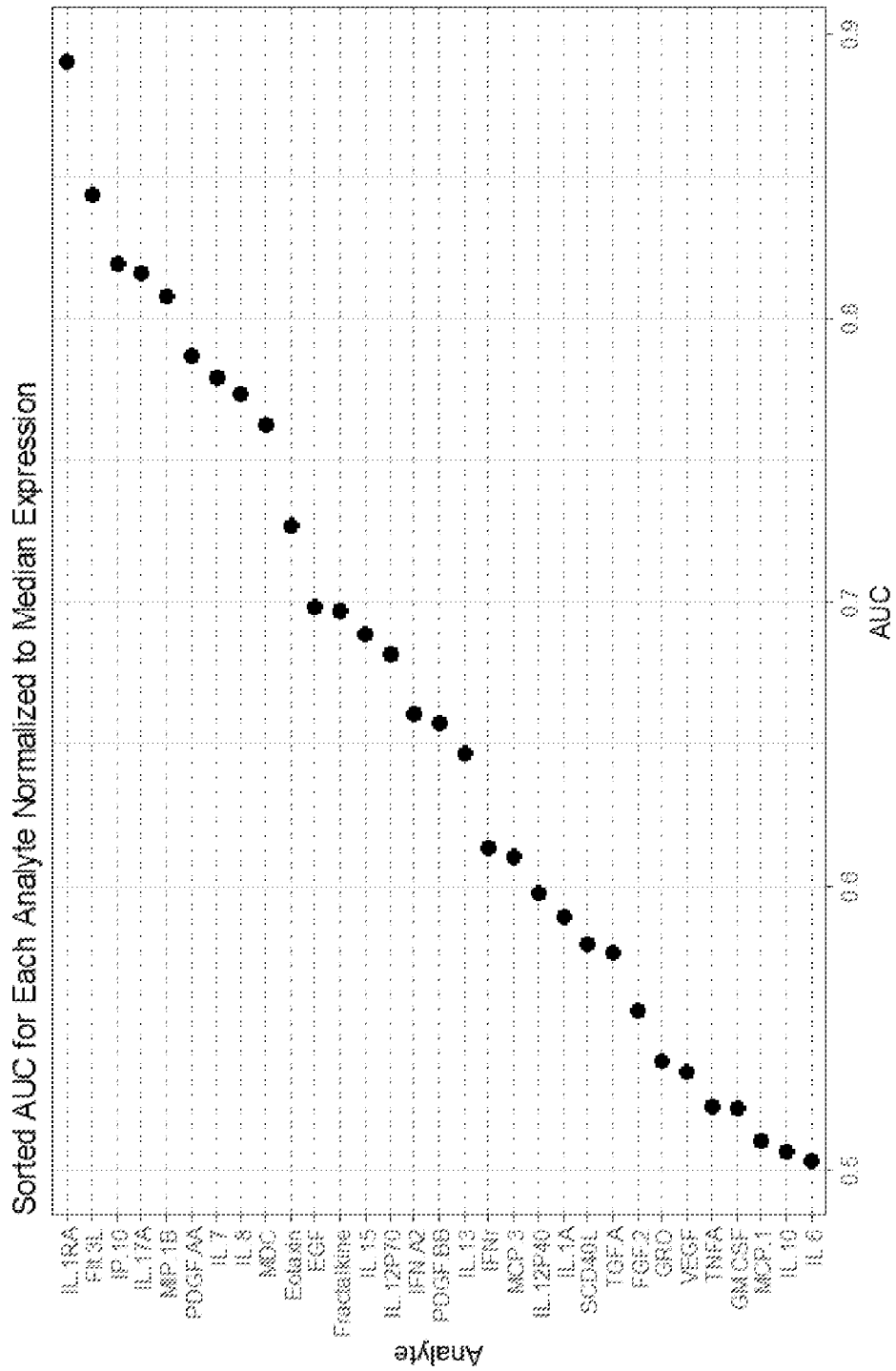
Figure 19:
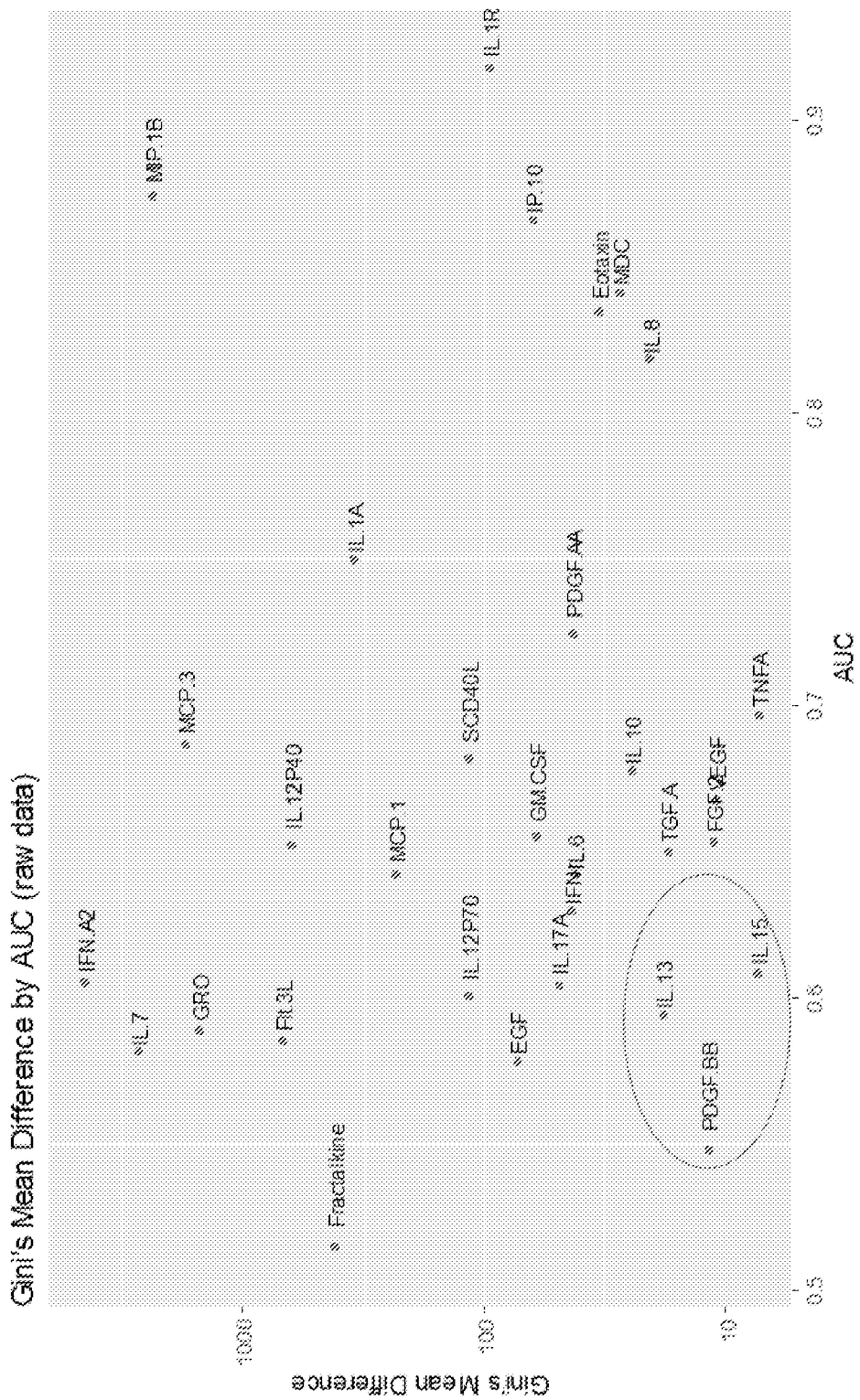
FIG. 19 shows a housekeeping analyte should (1) not be differentially expressed and (2) not change very much. These two criteria narrow the search to the lower left, in particular, the three analytes within the ellipse. The closest to the origin is PDGF-BB. Total protein concentration and median expression are differentially expressed. Total protein is higher in benign tissue.
Figure 20:
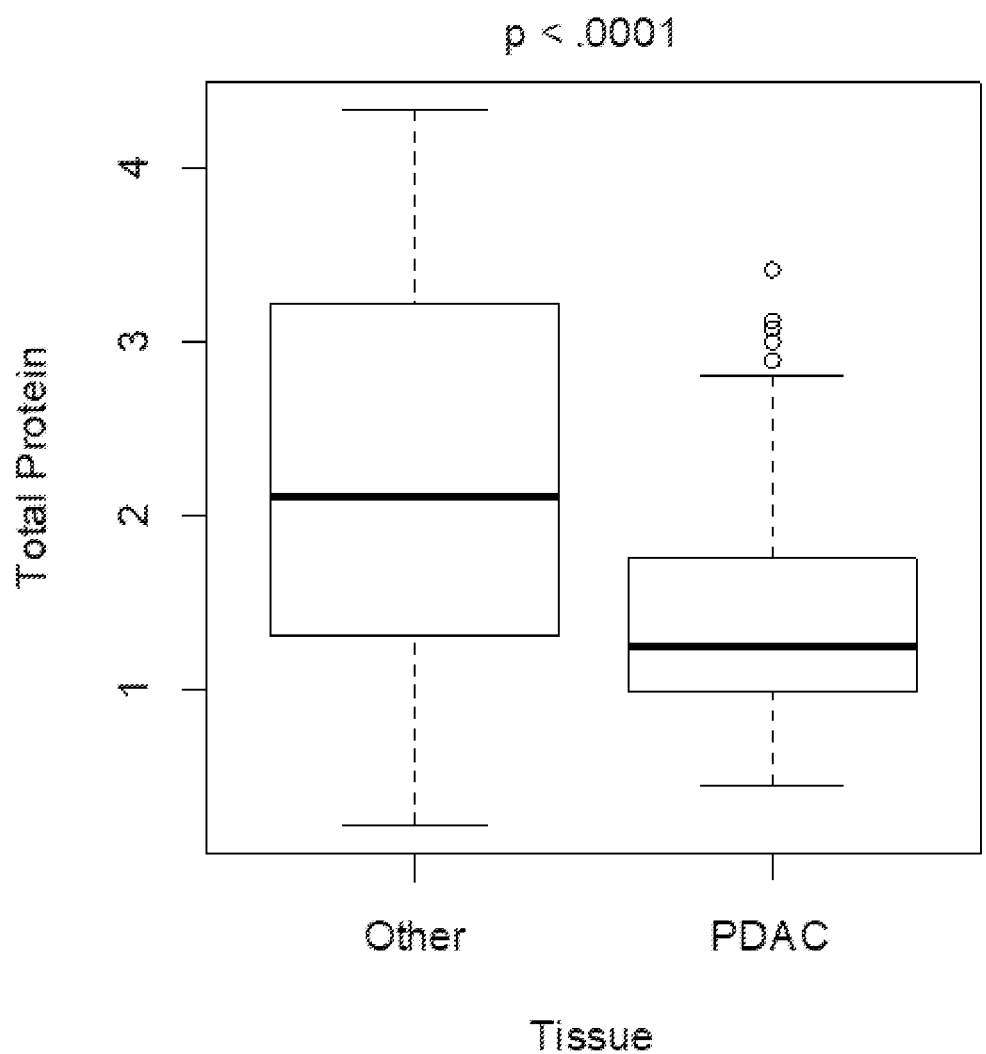
FIG. 20 shows total protein is inadequate to normalize PDAC data.

PPV and NPV values for the penalized logistic regression model optimized for accuracy were calculated across disease prevalence (FIGS. 14A and 14B). The prevalence of PDAC in patients undergoing EUS-guided FNA for pancreatic mass is 75-80% [Turner, B. G., et al., Gastrointest Endosc, 2010. 71(1):91-8; Shin, H. J., et al., Cancer, 2002. 96(3):174-80]. Our model provides for a PPV of 97-98% and NPV of 67-72% at this disease prevalence.

DISCUSSION

Improved diagnostic capability of EUS-guided FNA is critical to improving care for patients with PDAC. The above data demonstrate definite differences in the cytokines and chemokines present in the microenvironment of PDAC and benign pancreatic tissue. Univariate analysis found patterns of protein expression between the two tissues types. Based on multivariate analysis, these patterns may be able to be leveraged to distinguish between benign and malignant pancreatic tissue. Recursive partitioning and logistic regression modeling was able to classify tissue as PDAC or benign with a high degree of accuracy, sensitivity, and specificity. Further, the parameters of the model can be changed to optimize for a sensitivity or specificity of nearly 100%. This allows for the model to be used to either rule-in or rule-out disease based on needs of the practitioner. The prevalence of PDAC in patients undergoing EUS-guided FNA for pancreatic mass is 75-80% [Turner, B. G., et al., Gastrointest Endosc, 2010. 71(1):91-8; Shin, H. J., et al., Cancer, 2002. 96(3):174-80]. The disclosed model provides for a positive predictive value of 97-98% at this disease prevalence.

Other efforts to improve diagnostic yield have been proposed but have yet to gain clinical acceptance. Early efforts focused on immunostaining of a number of proteins including IMP3, S100, p53, and MIB-1 have yielded varied results and remain dependent of obtaining adequate specimens [Burnett, A. S., et al., J Surg Res, 2014. 190(2):535-47; Senoo, J., et al., Pancreatology, 2018. 18(2):176-183]. The source of the proteins detected by assay in this study is unclear, but it is possible that is from infiltrating immune cells in the tumor are the primary source. Because the protein signature proposed is composed of soluble proteins, it is possible that these cytokines and chemokines may be more ubiquitous in the tumor microenvironment and less dependent on obtaining sufficient malignant epithelial cells. Elastography has been suggested as an imaging adjunct to endoscopic ultrasound and measures stiffness of tissue, known as strain ratio. While useful in its sensitivity, it is currently limited by poor specifity around 70% [Kongkam, P., et al., J Gastroenterol Hepatol, 2015. 30(11):1683-9; Mei, M., et al., Gastrointest Endosc, 2013. 77(4):578-89]. As an adjunct to cytopathology in patients with pancreatic masses, these modalities are more useful if they rule-in disease with high specificity. MiRNA signatures also hold promise to improve the diagnostic accuracy of EUS-guided FNA with improved specificity of 85-95% at the cost of sensitivity of 81-83% [Brand, R. E., et al., Clin Gastroenterol Hepatol, 2014. 12(10):1717-23; Frampton, A. E., et al., Oncotarget, 2016. 7(19):28556-69]. The disclosed recursive partitioning model optimized to specificity yielded a specificity of 92.2%. When optimized to specifity, it improved to 98.4% with a decrease in sensitivity from 90.2% to 79.2%. RNA sequencing has been shown to distinguish malignant from benign lesions with high sensitivity (87%) but lower specificity (75%). It is important to note that inadequate RNA was obtained in 9 of the 48 enrolled subjects limiting this adjunct in a similar way to cytopathology. Finally, FISH and K-ras analysis may increase specificity of EUS-guided but further clinical trials are needed to validate these modalities and are not readily available at many centers [Reicher, S., et al., Pancreas, 2011. 40(7):1057-62; Fuccio, L., et al., Gastrointest Endosc, 2013. 78(4):596-608].

Protein signatures from the tumor microenvironment have been previously been explored in a number of cancers for a variety of purposes. Similar to PDAC, about 22% of FNAs from thyroid nodules yield indeterminate pathology [Yoon, J. H., et al., Ann Surg Oncol, 2011. 18(5):1282-9]. Many of these patients undergo unilateral thyroid lobectomy to determine pathology. Galectin-3, Hector Battiflora Mesothelial-1 (HBME-1), and CD44v6 have been proposed as molecular markers separately or in combination to improve the accuracy of FNA with sensitivity and specificity as high as 88% and 98%, respectively [Bartolazzi, A., et al., Lancet, 2001. 357(9269):1644-50; Cantara, S., et al., Int J Mol Sci, 2017. 18(4)]. Protein signatures in ovarian cancer have been proposed as serum biomarkers as well as to predict prognosis and chemosensitivity [Jin, C., et al., Int J Gynecol Cancer, 2018. 28(1):51-58; Muinao, T., et al., Exp Cell Res, 2018. 362(1):1-10; Trachana, S. P., et al., PLoS One, 2016. 11(6):e0156403]. Similar biomarker and prognostic markers have been proposed in lung cancer and breast cancer as well [Gocheva, V., et al., Proc Natl Acad Sci USA, 2017. 114(28):E5625-E5634; Lee, H. B., et al., Anticancer Res, 2015. 35(11):6271-9; Skoog, P., et al., PLoS One, 2017. 12(6):e0179775]. Additional investigation into protein signatures in PDAC may provide similar utility in prognosis and chemosensitivity and deserves investigation.

The disclosed study has a number of important limitations. It is a single-center retrospective analysis. Tissues were obtained at the time of surgical resection with sharp dissection, not EUS-guided FNA. Previous work demonstrated the ability to obtain high protein concentrations from FNA performed at the time of surgical resection but the idea EUS-guided FNA samples would provide reasonable tissue for protein profiling was speculative. Further, this study is limited to PDAC and benign specimens.

Failure to diagnose PDAC can have devastating consequences for patients. The disclosed work demonstrates unique soluble protein signatures within the tumor microenvironment of PDAC compared to benign tissue.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject for pancreatic ductal adenocarcinoma (PDAC), consisting of
    (a) assaying a tumor microenvironment sample from the subject for levels of soluble immune proteins consisting of Eotaxin, FGF-2, G-CSF, IL-4, IP-10, PDGF-AA, and TNFα;
    (b) calculating a survival score based on differential expression of the soluble immune proteins; and
    (c) wherein when the survival score is indicative of prolonged post-surgical survival, further comprising surgically resecting the PDAC from the subject;
    wherein the tumor microenvironment sample is a fine needle aspiration (FNA) biopsy of the PDAC,
    wherein levels of Eotaxin, FGF-2, IL-4, IP-10, and TNFα relative to control values are positively correlated to the survival score and levels of G-CSF and PDGF-AA relative to control values are negatively correlated to the survival score;

wherein the method is carried out in order as recited; and wherein following step (b), the method optionally includes normalizing an amount of detected soluble immune proteins to an amount of PDGF-BB or IL-15.

2. The method of claim 1, wherein the survival score is calculated using multivariate analysis.

3. The method of claim 1, wherein the subject received treatment with chemotherapy, hormone therapy, radiation therapy, or a combination thereof prior to step (a).

4. The method of claim 1, wherein the subject received treatment with portal vein resection prior to step (a).

5. The method of claim 1, wherein the subject does not have elevated serum CA19-9 levels.

6. The method of claim 1, wherein the subject has elevated serum CA19-9 levels.

* * * * *